(12) United States Patent
Essock et al.

(10) Patent No.: US 7,139,602 B2  
(45) Date of Patent: Nov. 21, 2006

(54) SHAPE ANALYSIS OF SURFACES

(75) Inventors: Edward A. Essock, Anchorage, KY (US); Michael J. Sinai, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 546 days.

(21) Appl. No.: 10/133,268

(22) Filed: Apr. 26, 2002

(65) Prior Publication Data

US 2003/0114740 A1 Jun. 19, 2003

Related U.S. Application Data

(60) Provisional application No. 60/286,654, filed on Apr. 26, 2001.

(51) Int. Cl.  
*A61B 5/05* (2006.01)

(52) U.S. Cl. .................................................. 600/407

(58) Field of Classification Search ............... 600/407; 250/363.01, 363.02, 363.03, 363.04; 606/1, 606/2

See application file for complete search history.

(56) References Cited

U.S. PATENT DOCUMENTS

| | | | |
|---|---|---|---|
| 5,713,364 A * | 2/1998 | DeBaryshe et al. | 600/476 |
| 5,715,821 A * | 2/1998 | Faupel | 600/302 |
| 5,800,350 A * | 9/1998 | Coppleson et al. | 600/372 |
| 6,258,576 B1 * | 7/2001 | Richards-Kortum et al. | 435/40.52 |
| 6,697,652 B1 * | 2/2004 | Georgakoudi et al. | 600/310 |

OTHER PUBLICATIONS

Bryant, F.D., et al., "An Extension of Fourier Analysis Techniques of Nerve Fiber Layer Measurements from Scanning Laser Polarimetry", *Investigative Ophthalmology and Visual Science, Suppl.*, vol. 41, No. 4, (Mar. 15, 2000), p. S92.

Essock, E.A., et al., "Detection of Glaucoma by Fourier Analysis of Polarimetry Data Using Discriminant Analysis", *Investigative Ophthalmology and Visual Science, Suppl.*, vol. 42, No. 4, (Mar. 15, 2001), P. S17.

Essock, E.A., et al., "Fourier Analysis of Nerve Fiber Layer Measurements from Scanning Laser Polarimetry in Glaucoma: Emphasizing Shape Characteristics of the 'Double-Hump' Pattern", *Journal of Glaucoma*, vol. 9, No. 6, (2000), pp. 444-452.

Essock, E.A., et al., "New Approaches to Analyzing Polarimetry Data", *Investigative Ophthalmology and Visual Science Suppl.*, vol. 40, No. 41, (Mar. 15, 1999), p. S660.

Sinai, M.J., et al., "Fourier Analysis of the RNFL in the Diagnosis of Glaucoma Using OCT and GDx", *Investigative Ophthalmology and Visual Science, Suppl.*, vol. 42, No. 4, (Mar. 15, 2001), p. S135.

* cited by examiner

*Primary Examiner*—Daniel Robinson  
(74) *Attorney, Agent, or Firm*—Viksnins Harris & Padys PLLP

(57) ABSTRACT

A method and apparatus are provided to map the shape or thickness of a surface. Thickness estimates across a distance are received, and Fourier analysis is performed to generate Fourier amplitude coefficients and phase values for a number of frequency components. Linear discriminant functions are used to characterize the resulting shape as normal or not. Discriminant functions are provided that aid in the diagnosis of glaucoma when the thickness measured is the retinal nerve fiber layer thickness.

10 Claims, 23 Drawing Sheets

SHAPE ANALYSIS OF SURFACES

RELATED APPLICATION

This application claims priority to U.S. Provisional Patent Application No. 60/286,654, filed Apr. 26, 2001, the entirety of which is incorporated herein by reference.

BACKGROUND

Many conditions and diseases are associated with abnormalities of a surface. The existence and severity of the condition can be diagnosed by plotting data measurements of thickness of the surface layer, that is, height from a chosen base layer and comparing the results to a normal surface, that is, one that is not diseased. These conditions may include coronary artery disease, abnormal angiogenesis as in diabetic retinopathy and blood vessel thrombi. The eye disease glaucoma, a leading cause of blindness, is characterized by alterations in the retinal nerve fiber layer.

It is well known that the necessary point measurements can be obtained by scanning laser polarimetry (SLP), ocular coherence tomography (OCT), ultrasound, photogrammetry or the like. However, the reliability and power of such methods are dependant on the mathematical analysis of the data. Some previous methods selected a normal value for the thickness of the surface in question and determined individual variations from normal values.

DESCRIPTION OF EMBODIMENTS

Figure 1:
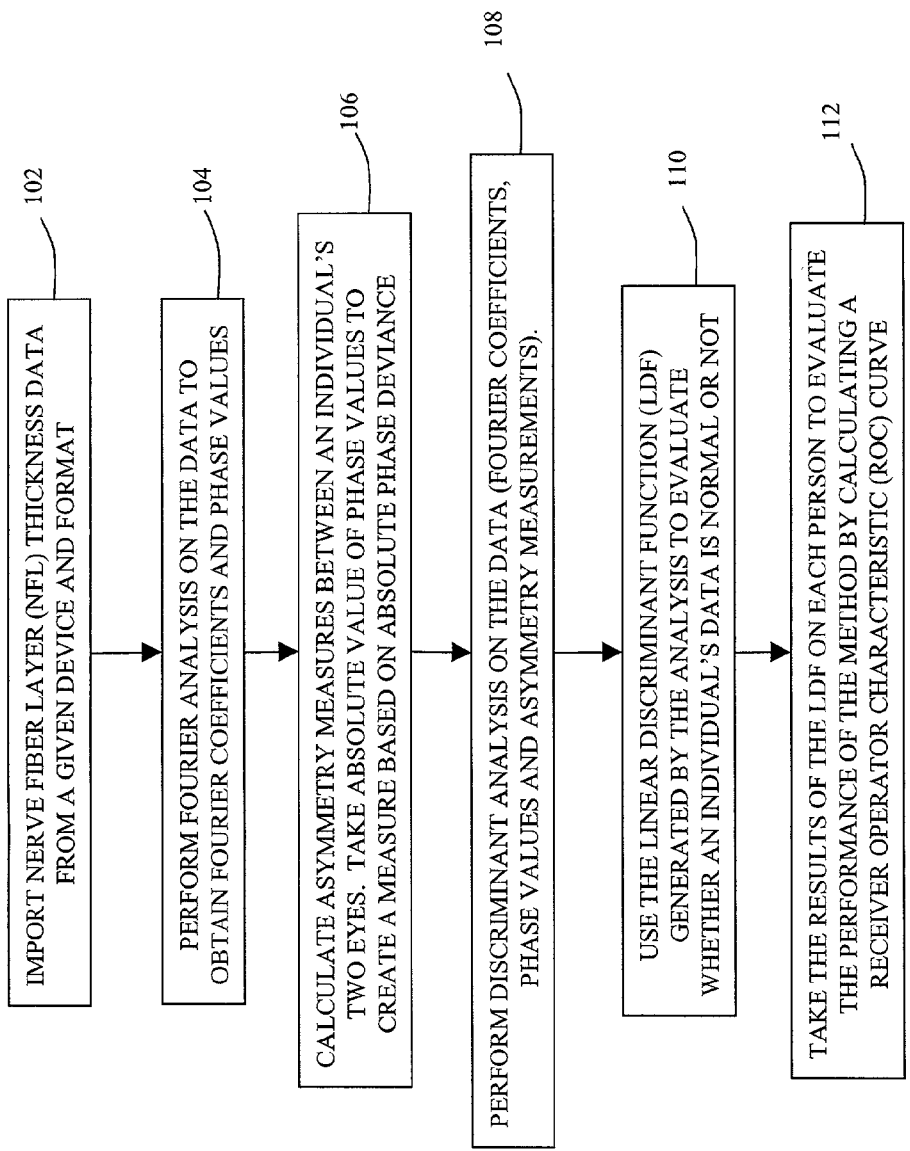
FIG. 1 shows a flowchart that describes various method embodiments of the invention.

In the following detailed description, reference is made to the accompanying drawings that show, by way of illustration, specific embodiments in which the invention may be practiced. It is to be understood that various embodiments of the invention, although different, are not necessarily mutually exclusive. For example, a particular feature, structure, or characteristic described herein in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted along with the full range of equivalents to which the claims are entitled. In the drawings, like numerals refer to the same or similar functionality throughout the several views.

In various embodiments of the present invention, the shape of a distribution of measurements of a surface area is determined by scanning the surface with a measuring system and applying mathematical analyses to the resulting data points in order to map the surface. The measuring system may be a scanning laser polarimeter (SLP), an ocular coherence tomograph (OCT), or any other device capable of measuring the shape of a surface area. Such devices may be of the appropriate size for the surface to be analyzed and may be fitted with access mechanisms such as fiber optic cannulae for such surfaces that are not readily accessible.

The shape of the distribution of measurements form a graph of the particular measured value plotted across distance. The mathematical analysis is directed at characterizing the shape of the distribution of measurements across the surface. Various methods analyze shape in part by obtaining amplitude and phase values using a Fourier transform. In some embodiments of the invention, these factors are then combined in a linear discriminant function or other methods, and the resultant value(s) is then used to distinguish one group of surfaces from another, that is, diseased from normal. The use of embodiments of the invention in the diagnosis of glaucoma is described in detail.

FIG. 1 shows a flowchart that describes various method embodiments of the invention. Some embodiments of the invention generate Fourier-based discriminant functions for the diagnosis of glaucoma. Other embodiments of the invention use the Fourier-based discriminant functions to aid in the diagnosis of glaucoma. FIG. 1 represents embodiments that generate Fourier-based discriminant functions, as well as embodiments that use Fourier-based discriminant functions. Each of the actions in the flowchart are described briefly here, and are described in more detail in later portions of this description.

In block 102, nerve fiber layer (NFL) thickness data are imported from a given device and format. As previously described, the device may be a scanning laser polarimeter (SLP), an ocular coherence tomograph (OCT), or any other device capable of measuring the shape of a surface area or the thickness of the NFL. The data may also be of any suitable format. Examples include, but are not limited to, a complete mapping of the NFL thickness in rectangular or polar coordinates, or a partial mapping. Partial mappings may include hemiretinal NFL measurements, NFL measurements of quadrants of the eye, or any other subset of a complete NFL thickness mapping. Some embodiments described in more detail below include NFL thickness measurements within an annular region (or "ring") of the NFL at a given radius from the center of the optical disc. Other suitable formats include data that is partially processed. For example, in some embodiments, imported data may be a set of NFL thickness averages, where each average represents the average thickness over a defined region of the eye.

In block 104, a Fourier transform is applied to the data to yield Fourier coefficients and phase values. In some embodiments, the Fourier transform is applied using a discrete Fourier transform (DFT), and in other embodiments, the Fourier transform is applied using a fast Fourier transform (FFT). Any number of Fourier coefficients and phase values can be generated without departing from the scope of the invention. The Fourier transform can be applied to NFL thickness data representing the entire eye, or a portion thereof. For example, in some embodiments of the invention, the Fourier transform is applied to data representing each hemiretina separately, and in other embodiments, the Fourier transform is applied to data representing a ring about the whole retina.

In block 106, asymmetry measures are calculated between an individual's two eyes. The asymmetry may utilize any portion of the coefficients and phase values generated in block 104 or may utilize other information. In some embodiments, asymmetry measures between portions of the same eye are calculated. The phase values generated in block 104 can be useful in many different forms. As shown in block 106, the absolute value of the phase of each of the Fourier components can be taken to create a measure based on absolute phase deviance.

In block 108, a discriminant analysis is performed on the Fourier coefficients, phase values, and asymmetry measurements to create measures to aid in the diagnosis of glaucoma. In some embodiments, a stepwise discriminant analysis is used so that variables that contribute significantly to the function are included.

In block 110, the linear discriminant function generated in block 108 is used to evaluate whether an individual's data is normal or not. In some embodiments, block 110 corresponds to using the result of the discriminant analysis to aid in the diagnosis of glaucoma.

In block 112, the results of the linear discriminant function are evaluated by calculating a receiver operator characteristic (ROC) curve. This is useful in some embodiments when determining linear discriminant functions to be used with future populations. ROC curves can be compared against each other to determine linear discriminant functions to be used. In other embodiments, actions represented by this block are not performed. For example, when the linear discriminant function has been chosen and is not being evaluated for efficacy, the actions of block 112 can be omitted.

Figure 2:
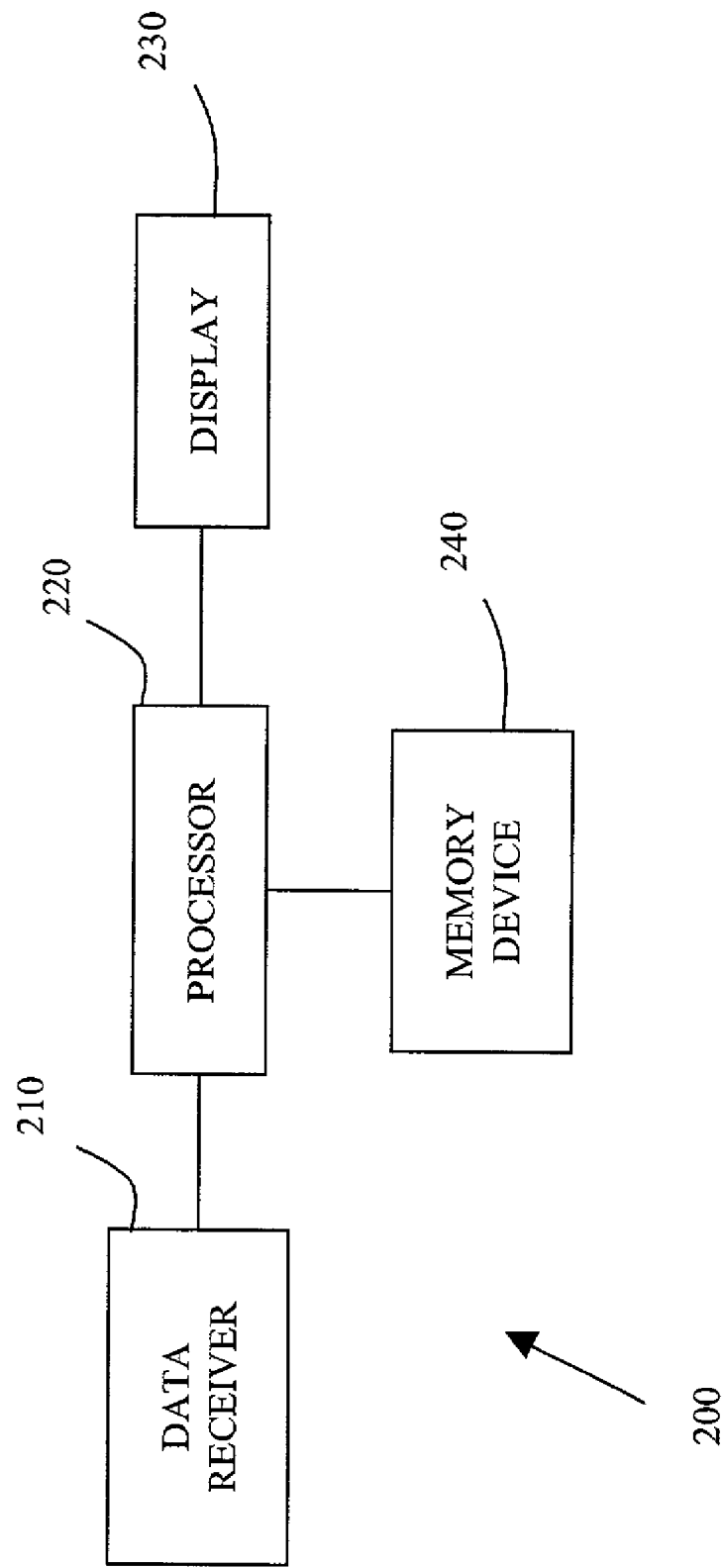
FIG. 2 is a diagram of an apparatus in accordance with various embodiments of the invention.

FIG. 2 shows a block diagram of an apparatus in accordance with various embodiments of the invention. Apparatus 200 includes data receiver 210, processor 220, memory device 240, and display 230. Data receiver 210 is a device capable of receiving data representing the shape or thickness of a surface. For example, data receiver 210 may be an interface circuit that interfaces to an SLP or OCT device as previously described. Also for example, data receiver 210 may be an SLP or OCT device that measures NFL thickness data directly.

Processor 220 is a computing device that is capable of performing the method embodiments of the present invention. For example, referring now back to FIG. 1, processor 220 may perform the actions listed in the various blocks. In a clinical setting, processor 220 may receive NFL thickness data from data receiver 210, perform Fourier analysis on the data, and then apply measures and discriminants to the data to aid in the diagnosis of glaucoma. In a research setting, processor 220 may also perform a linear discriminant analysis to generate linear discriminant functions, and then generate receiver operator curves (ROC) to display the efficacy of the various discriminants.

Processor 220 may be any type of processor suitable to perform actions to support the operation of apparatus 200. For example, processor 220 may be a microprocessor, a microcontroller, or the like. Also for example, processor 220 may be a hardware controller or a collection of hardware controllers that perform specific tasks. Also, in some embodiments, processor 220 is embedded in a measurement device such as an SLP or OCT device. Further, processor 220 may be a commercially available processor embedded in a computer, such as a personal computer (PC).

Display 230 is an apparatus capable of displaying results from processor 220. In some embodiments of the invention, display 230 is a video monitor capable of graphically displaying information regarding measurements, Fourier analysis, and the like. In other embodiments, display 230 is a simpler device that displays the results of applying discriminant functions. For example, display 230 may be a small printer that prints out numerical information relating to results. In some embodiments, the display provides a diagnosis based on the preceding analysis. In other embodiments, display 230 does not provide a diagnosis, but instead provides information to aid in the diagnosis, and the diagnosis is left to personnel operating apparatus 200.

Memory device 240 represents an article that includes a machine-accessible medium. For example, the memory may represent any one or more of the following: a hard disk, a floppy disk, random access memory (RAM), read only memory (ROM), flash memory, CDROM, or any other type of article that includes a medium readable by a machine. The memory may store instructions for performing the execution of the various method embodiments of the present invention. The memory may also store NFL thickness data, results from discriminant analysis, and other information in support of the various method embodiments of the present invention.

This disclosure, while it applies to any type of shape, describes in detail multiple methodologies of detecting glaucoma through shape analysis of nerve fibers in the eye. The remainder of this disclosure is organized to describe: 1) different nerve fiber layer measurements; 2) Fourier analysis of those measurements; and 3) different measures and discriminants that utilize information generated by the Fourier analysis. Experimental results are also described from studies performed using a few representative embodiments of the invention.

Nerve Fiber Layer Measurements

Since glaucoma leads to characteristic damage of the retinal ganglion cells, strategies for the detection of glaucoma often focus on detecting the functional or structural changes associated with ganglion cell disruption. Computer-assisted imaging technologies for detection of the neural structural defects associated with glaucoma that are based on topography of the retinal nerve fiber layer (NFL) offer promise for detecting and assessing glaucomatous disruption. Multiple clinical tools are available for objective quantitative assessment of the NFL. Examples include, but are not limited to, a scanning laser polarimeter such as the GD x device (Laser Diagnostic Technologies, Inc. San Diego, Calif.) or the ocular coherence tomograph (OCT, Zeiss-Humphrey, Dublin Calif.). Other devices capable of measuring the shape of a surface area may also be used.

The scanning laser polarimeter infers NFL thickness based on optical properties of the NFL. When polarized light is projected through a birefringent structure such as the nerve fiber layer, it undergoes a shift, or retardation, in polarization. The amount of shift is dependent upon the thickness of the structure, with a greater shift implying a higher thickness. The polarimeter measures retardation to provide an indication of the thickness of the nerve fiber layer around the optic disc after compensating for retardation from other structures (e.g., cornea). The ocular coherence tomograph infers thickness based on measurements of the time-course of back-scattered light.

Nerve fiber layer measurements can be made on an entire eye, or on a subset of an eye. For example, in some embodiments of the invention, nerve fiber thickness data is collected and analyzed for each hemiretina (superior and inferior) of an eye. In other embodiments of the invention, nerve fiber thickness data is collected and analyzed for the entire retina of each eye. In still further embodiments, measurement data representing both hemiretina and the entire eye are collected and analyzed.

Some embodiments of the present invention utilize measurement information gathered for a circular region defined by a ring around the optic disc. The ring may have any diameter, and also may be divided into angular sectors for analysis. Various embodiments of the invention utilizing rings about the optic disc are described further below.

Entire Retina NFL Measurement

Figure 3:
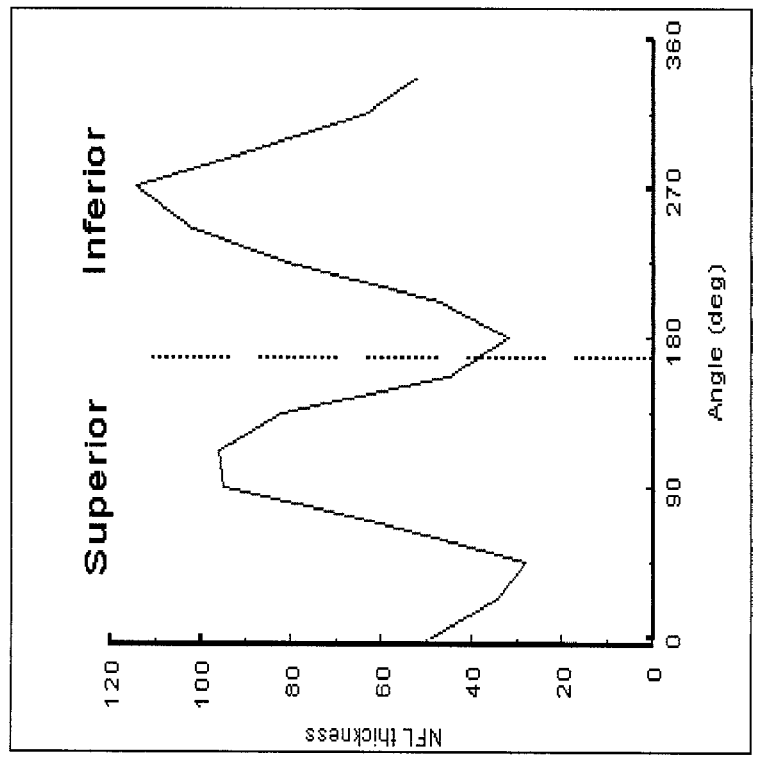
FIG. 3 shows a first plot of a "double hump" pattern of nerve fiber layer thickness values obtained from a circular ring around a retina.
Figure 5:
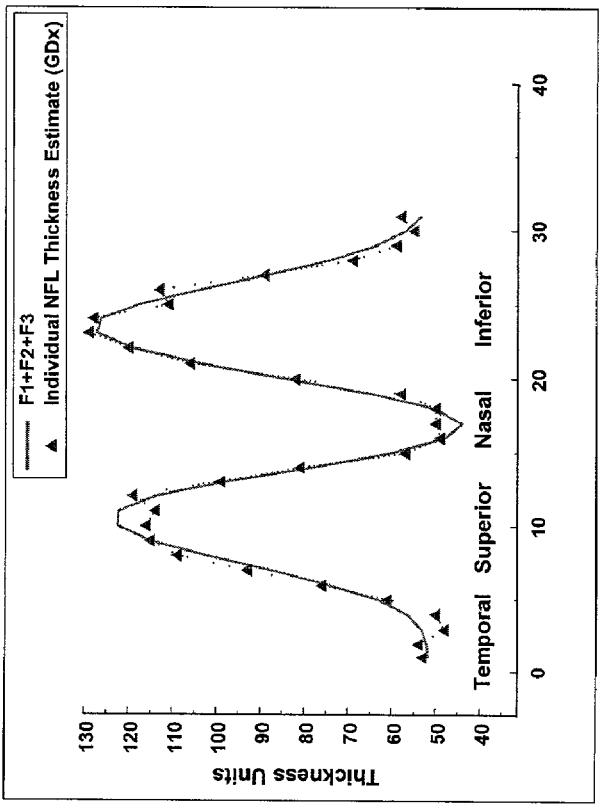
FIG. 5 shows a second plot of a "double hump" pattern of nerve fiber layer thickness values obtained from a circular ring around a retina.

FIGS. 3 and 5 show two characteristic "double hump" patterns of NFL thickness values obtained from a circular ring around the retina. The double-hump pattern represents a full 360° pattern around the retina. As shown in FIG. 3, 16 NFL thickness values are plotted as a function of degrees around the retina. The first 180° represent the superior hemiretina, and the last 180° represent the inferior hemiretina. The superior hemiretina and the inferior hemiretina are divided by a vertical dashed line.

As shown in FIG. 5, 32 NFL thickness values are plotted to show the superior and inferior hemiretinas. FIG. 5 is also labeled to indicate the temporal and nasal portions of the plot. The double-hump pattern of FIG. 5 is not plotted as a function of degrees, but instead is shown as a function of distance numbers used in the Fourier analysis (described below). Notwithstanding the labeling of the plot in FIG. 5, the double hump pattern represents substantially 360° around the retina.

Both FIGS. 3 and 5 show NFL thickness data gathered for the circular region defined by a 1.7 disc diameter ring (a distance of 0.85 disc diameters from the disc margin). The ring in FIG. 3 is divided into 16 angular sectors of 22.5° each. The ring in FIG. 5 is divided into 32 angular sectors of 11.25° each. These diameters and numbers of angular sectors are representative, and are not a limitation of the invention. For example, in some embodiments of the invention, rings having a diameter other than 1.7 disc are utilized. Also for example, although FIGS. 3 and 5 have 16 and 32 samples, respectively, any number of samples can be taken, and therefore, the ring can be divided into any number of angular sectors.

Hemiretina NFL Measurement

As described above with reference to the entire retina NFL measurement, the hemiretina NFL measurement corresponds to substantially 180° of arc around the optic disc. FIG. 3 shows the superior and inferior hemiretinas divided by a dashed line. In some embodiments of the invention, hemiretina data is collected separately for each hemiretina in each eye. In other embodiments, NFL thickness data is collected for the full retina as described above, and the analysis is performed on a hemiretina-by-hemiretina basis.

Analysis on separate hemiretinas rather than on the full 360° pattern can be useful in part because the superior and inferior nerve bundles are not located exactly 180° apart and also in part because this allows asymmetrical (superior vs. inferior) changes within a retina to be assessed.

Each data point shown in FIGS. 3 and 5 can be a result of a single measurement, or can be an average of multiple measurements. For example, within an angular sector bounded by the edges of a ring, multiple measurements may be made and averaged. In some embodiments of the invention, the averaging of multiple measurements occurs in the device performing the measurement, such as an SLP device or OCT device, and in other embodiments, the measuring device provides raw data having multiple measurements which are then averaged separately.

Fourier Analysis of Nerve Fiber Layer Measurements

Various embodiments of the present invention emphasize the holistic shape of the pattern of NFL thickness variation across many locations, rather than local thickness per se. Fourier analysis is used to take into account the whole shape of the bi-modal "double-hump" distribution of nerve fiber layer thickness around the optic disc. The analysis is based on many local measurements and emphasizes the relative differences (such as rate of change) between areas. That is, rather than emphasizing thickness itself, which is known to vary widely among normals, measures made possible by Fourier analysis emphasize characteristics that typify the shape of the distribution of thickness in normals, while substantially ignoring variation of absolute thickness level. Various embodiments of the present invention achieve this by analyzing the pattern of the distribution of the NFL thickness and comparing this pattern in normals and glaucoma patients to aid in distinguishing glaucomatous eyes from normal eyes.

Fourier analysis is a mathematical procedure whereby a complex waveform pattern can be broken down (i.e., analyzed) into a set of harmonically related sine-waves of specified frequencies, amplitudes, and phases, which, when added together point for point, reproduce the original waveform. The lowest frequency component, referred to herein as the "fundamental," corresponds to the basic form of the pattern, and the harmonics are sine-waves whose frequencies are integer multiples of the fundamental (e.g., the second harmonic has a frequency that is two times that of the fundamental).

The textbook *Wavelets and Subband Coding* by Martin Vetterli and Jelena Kovačević (Prentice Hall PTR, Upper Saddle River, N.J.), which is hereby incorporated by reference, teaches in detail the computation of fast Fourier Transform (pp. 337–341).

Any waveform (e.g. the "double hump" pattern of nerve fiber distribution) can be analyzed as a sum of sinusoidal components of various frequencies through Fourier analysis. Fourier analysis provides the amplitude and phase of the sinusoidal components that (additively) constitute a particular waveform; that is, a linear analysis in which the composite pattern is broken down into a set of components which, when added point by point, yield the original pattern.

Fourier Analysis of Hemiretinal Measurements

Figure 4:
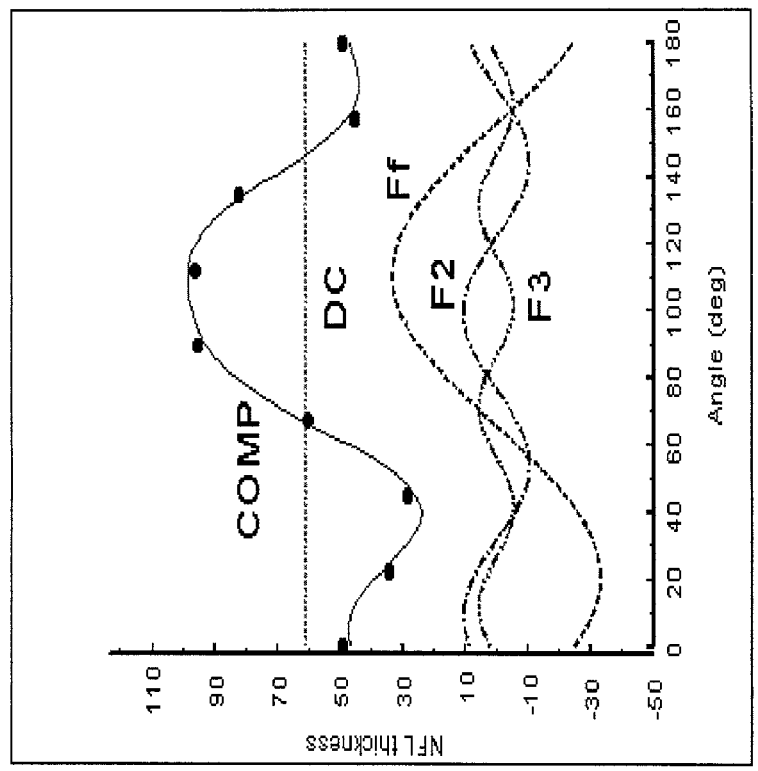
FIG. 4 shows a plot of the result of a Fourier analysis of the superior hemiretina NFL thickness data shown to the left of the dashed vertical line in FIG. 3.

FIG. 4 shows the result of a Fourier analysis of the superior hemiretina NFL thickness data shown to the left of the dashed vertical line in FIG. 3. In FIG. 4, the eight data points from the superior hemiretina are plotted as solid points. The dark solid line plotted with the data points shows the resultant curve fit to the data by Fourier analysis. The curve is formed by the point-to-point addition of the other four curves plotted: the fundamental frequency (Ff); the second harmonic (F2), which is at twice the frequency of the fundamental; the third harmonic (F3), which is at three times the frequency of the fundamental, and the DC component.

As shown in FIG. 4, Fourier analysis was applied to one half of the "double hump" pattern of thickness values (i.e., a hemiretina) obtained at a disc diameter of 1.7. Thus, the Fourier analysis provides a set of sine-waves such that the amplitude of each indicates the relative contribution of that spatial scale to the shape of the composite curve fitting the NFL measurements (see FIG. 3). For example, if the NFL pattern was a pure sine-wave, the curve would be perfectly described by the fundamental and all other coefficients would be zero. Since the NFL shape is not sinusoidal, the harmonics serve to "shape" the fundamental so that the composite curve shape matches the NFL pattern. FIG. 4 illustrates how the addition of the Fourier components shape the composite curve to better fit the data.

Each of the curves shown in FIG. 4 includes attributes such as amplitude and phase. For example, the amplitude of the fundamental is the greatest, and the amplitudes of the second and third harmonics are smaller than the amplitude of the fundamental. Phase values generated by the Fourier analysis described phase offsets of each of the Fourier components. For example, the fundamental component and the first and second harmonics each have different phase offsets. The various Fourier component amplitude and phase values are useful when generating discriminant functions to aid in the diagnosis of disease.

Fourier Analysis of Entire Retina Measurements

Figure 6:
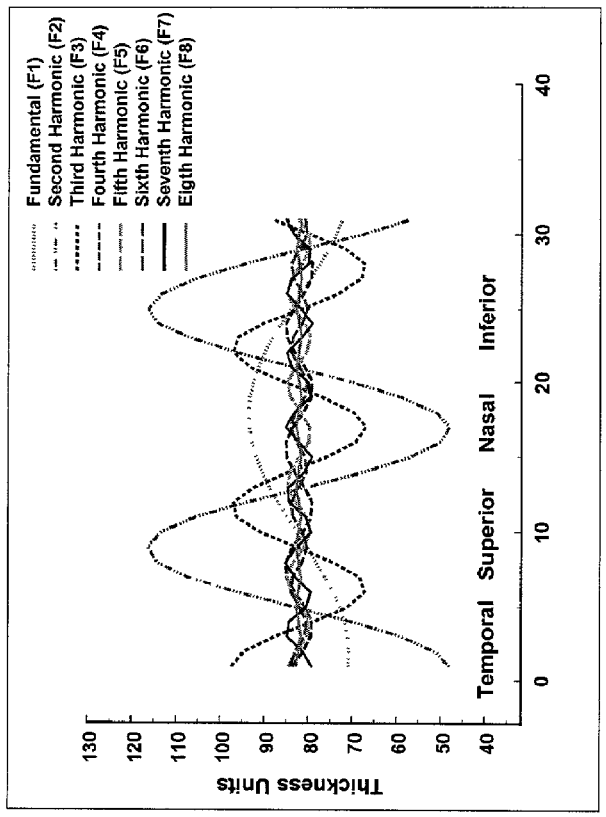
FIG. 6 shows a plot of the result of a Fourier analysis of the entire double-hump pattern shown in FIG. 5.

FIG. 6 shows the result of a Fourier analysis of the entire double-hump pattern shown in FIG. 5. The sum of the first three Fourier components of FIG. 6 are shown superimposed on the double-hump pattern in FIG. 5. As higher order Fourier components are summed in to the curve shown in FIG. 5, a better curve fit is obtained. The Fourier analysis of the double-hump patter of FIG. 5 yields nine waveforms in FIG. 6: the fundamental component, and the first eight harmonic components. Each component is characterized by attributes such as amplitude and phase. As described further below, the attributes of the various Fourier components can be utilized can be useful to aid in the diagnosis of disease.

Measures and Discriminants

Various embodiments of the present invention use discriminant measures based on the attributes of Fourier components for the superior and inferior hemiretinas and also full retinas of the left and right eyes for both the normals and glaucoma patients.

Discriminant measures include:

Ffund: the amplitude of the fundamental Fourier component; roughly analogous to the amplitude of the basic sinusoidal nature of the NFL distribution in a hemiretina.

Fsum: the sum of amplitudes of all or a subset of Fourier components (fundamental and harmonics); roughly corresponding to the composite amplitude of the whole shape of the periodic waveform in a hemiretina. p0 FasymW/in: the superior/inferior intraocular asymmetry within an eye in the amplitude of the Fsum measure. To avoid including eyes with an asymmetry due to a greater than normal amount of nerve fibers, some embodiments of the invention also require that at least one Fsum value (either superior or inferior value) also satisfies a threshold value.

FasymBet: the interocular asymmetry of the overall thickness (Fourier DC component). Like the FasymW/in measure, some embodiments of the invention also require that one of the Ffund values is also below a specified value.

FasymCoeff: an asymmetry measure calculated based on a ratio between the two eyes for each coefficient value from a full retinal Fourier analysis. The amplitude of each coefficient from one eye is compared against the amplitude of the corresponding coefficient from the other eye to yield asymmetry measures that quantify the interocular asymmetry of each Fourier component separately.

Logical OR Composite: to form a composite measure, any or all of the above measures may be combined by a "logical OR". That is, an eye may be classified as glaucomatous if it is deviant on any one of the contributing single measures.

Linear Discriminant Analysis: a linear discriminant function is generated using the Fourier amplitude and phase coefficients obtained from a full retinal analysis. Any combination of amplitude coefficients, phase values, interocular asymmetry measures, and intraocular asymmetry measures are entered into a discriminant analysis, and linear discriminant functions of the significant terms are generated.

In some embodiments, the discriminant analysis is a stepwise discriminant analysis.

As illustrated in the following experimental studies, the above measures and discriminants can be combined and modified in the various embodiments of the invention. As previously stated, the present invention encompasses the methods and apparatus used to generate the appropriate measures and discriminants, and also encompasses the use of the various measures and discriminants in a clinical setting to aid in diagnoses.

Experimental Studies

Multiple studies are now described. Each study utilizes various embodiments of the invention to aid in the diagnosis of glaucoma. The patient populations within the studies are described, as are the types of measurements made on those patients. Also described are the Fourier analyses applied, and the various measures and discriminants used to aid in the diagnosis.

Study Number 1: Fourier Analysis of Hemiretinal Data from a Single Population

Sixty eight volunteers (thirty four normals and thirty four glaucomatous patients) from the Louisville, Ky. area participated in the study. Both eyes were used in the analysis for all the normals and glaucoma patients. Ages ranged from 40–84 with a mean age of 53.5 (s.d.=9.8) for normals and 69.4 (s.d.=10.4) for glaucoma patients. All participants underwent ophthalmologic exams and no evidence of ocular pathology was found for the normals. All thirty four patients were diagnosed as having open angle glaucoma with no other ocular pathology. All glaucoma patients had been drawn from a glaucoma clinic and had some degree of glaucomatous field loss in both eyes. Visual fields were tested within 6 months of imaging with the Humphrey perimeter in sixty two eyes using the 30-2 threshold test. For the remaining six eyes with advanced glaucoma, the visual field testing had been performed with the 10-2 threshold test. An eye was classified as having glaucoma if the Humphrey glaucoma hemifield test was abnormal, the corrected pattern standard deviation was outside 95% normal limits, or a repeated cluster of 3 or more points was depressed at the 5% level on the pattern deviation plot. The average mean deviation (MD) for the 62 glaucomatous eyes who performed the 30-2 test was −8.9 dB. Only eight out of those 62 eyes had MD greater than −15 dB and were thus classified as having advanced glaucoma along with the six eyes that performed 10-2 visual field test (14 eyes total).

Retinal Imaging

Retinal thickness measures were obtained using a scanning laser polarimeter (Laser Diagnostic Technologies, Inc., San Diego). A retardation map was created by directing the scanning beam across a 15° field of view, producing a 256×256 pixel image approximately centered on the optic disc. Three images of each eye were obtained and averaged to create baseline images that were analyzed further. Degrees of retardation were converted into microns by a conversion factor of 1° of retardation per 7.4 microns. However, these thickness estimates are referred to herein as "thickness units" (t.u.) in part because of the approximate nature of the conversion to microns.

Data Analysis

Thickness values (in t.u.) were obtained by extracting a ten pixel wide circular region ("ring") at a specific distance from the optic disc and dividing it into sixteen angular sectors. Each of the sixteen sectors was 22.5° wide and labeled with the lower bound (0° to 337°). Thickness values were averaged for the pixels within each sector of the ring creating one thickness estimate for each region. Thus, for each 10 pixel wide ring, there were sixteen measures of thickness for each eye, with 8 from the superior hemiretina and 8 from the inferior hemiretina. Although sixteen sectors were chosen for analysis, any number of sectors can be analyzed by dividing the ring differently. The Fourier measures were calculated for the circular region defined by the 1.7 disc diameter ring (a distance of 0.85 disc diameters from the disc margin). The Fourier analyses were also performed on diameters other than 1.7 and were found to produce similar results.

Fourier analysis was applied to one half of the "double hump" pattern of thickness values (i.e., a hemiretina) obtained at a disc diameter of 1.7. Thus, each Fourier analysis provided a set of sine-waves such that the amplitude of each indicated the relative contribution of that spatial scale to the shape of the composite curve fitting the NFL measurements. For example, if the NFL pattern was a pure sine-wave, the curve would be perfectly described by the fundamental and all other coefficients would be zero. Since the NFL shape is not sinusoidal, the harmonics serve to "shape" the fundamental so that the composite curve shape matches the NFL pattern.

The pattern of the thickness measurements for the eight values of a hemifield were analyzed to get the Fourier amplitude coefficients (calculated as the square root of the sum of the squares of the real and imaginary part of each Fourier coefficient). The FFT analysis of a sequence of 8 numbers results in five unique coefficient values: the direct current (DC) value (analogous to the overall mean or a scaling factor), the fundamental, the second harmonic, the third harmonic and the fourth harmonic components. Various discriminate measures were developed based on these Fourier coefficients for the superior and inferior hemiretinas of the left and right eyes for both the normals and glaucoma patients. The associated ROC curves and the area under the curves were calculated by stepping through each cutoff value and noting the number of correct detections and false alarms for our sample.

We used several measures that were based on the Fourier coefficients: the amplitude of the fundamental Fourier component ($F_{fund}$), roughly analogous to the amplitude of the basic sinusoidal nature of the NFL distribution in a hemiretina; $F_{sum}$, the sum of amplitudes of the first four Fourier components (fundamental, second harmonic, third harmonic and fourth harmonic), roughly corresponding to the composite amplitude of the whole shape of the periodic waveform in a hemiretina; the superior/inferior asymmetry within an eye in the amplitude of the $F_{sum}$ measure, $F_{asymW/in}$; and the interocular asymmetry of the overall thickness (Fourier DC component), $F_{asymBet}$. (In this latter measure, the DC measure was used rather than the $F_{sum}$ measure in order to capitalize on the greater inter-eye asymmetry of the measure.) To form composite measures, these measures were combined by a "logical OR". That is, an eye was classified as glaucomatous if it was deviant on any one of the contributing single measures. To determine the cut-off values for dividing glaucoma from normal, the value under consideration (or values on each single measure in the case of a composite measure) was systematically adjusted until the value that maximized the sum of the sensitivity and specificity was found.

The results below describe the analysis which proceeded in several steps. First the utility of the fundamental component of the Fourier analysis alone were assessed, and then the additional Fourier components and the symmetry comparisons (hemifield or eyes) of Fourier measures were sequentially added to consider different composite measures. For each of these measures the sensitivity and specificity was calculated and then compared for the different measures as well as for standard GDx® analysis (see Table 1).

TABLE 1

| Diagnostic Measure | Sensitivity (%) | Specificity (%) |
|---|---|---|
| Fundamental alone ($F_{fund}$) | 77% | 91% |
| Sum of the Fourier amplitudes alone ($F_{sum}$) | 75% | 91% |
| $F_{fund}$ and $F_{sum}$ combined | 84% | 90% |
| $F_{fund}$, $F_{sum}$, $F_{asymW/in}$, and $F_{asymBet}$ combined | 96% | 90% |
| GDx ® number | 85% | 91% |

Independent-groups t-tests were used to compare the groups of normal and glaucoma subjects whenever possible (i.e., for the $F_{fund}$ and $F_{sum}$ measures). The Fourier coefficients for the glaucoma patients and normal subjects were compared statistically with a 2×4×2×2 mixed design MANOVA (patient category×Fourier coefficients×eye× hemiretina). A significance level of 0.05 was adopted for all tests and the Wilks F values were used to determine significance.

Results

Figure 7:
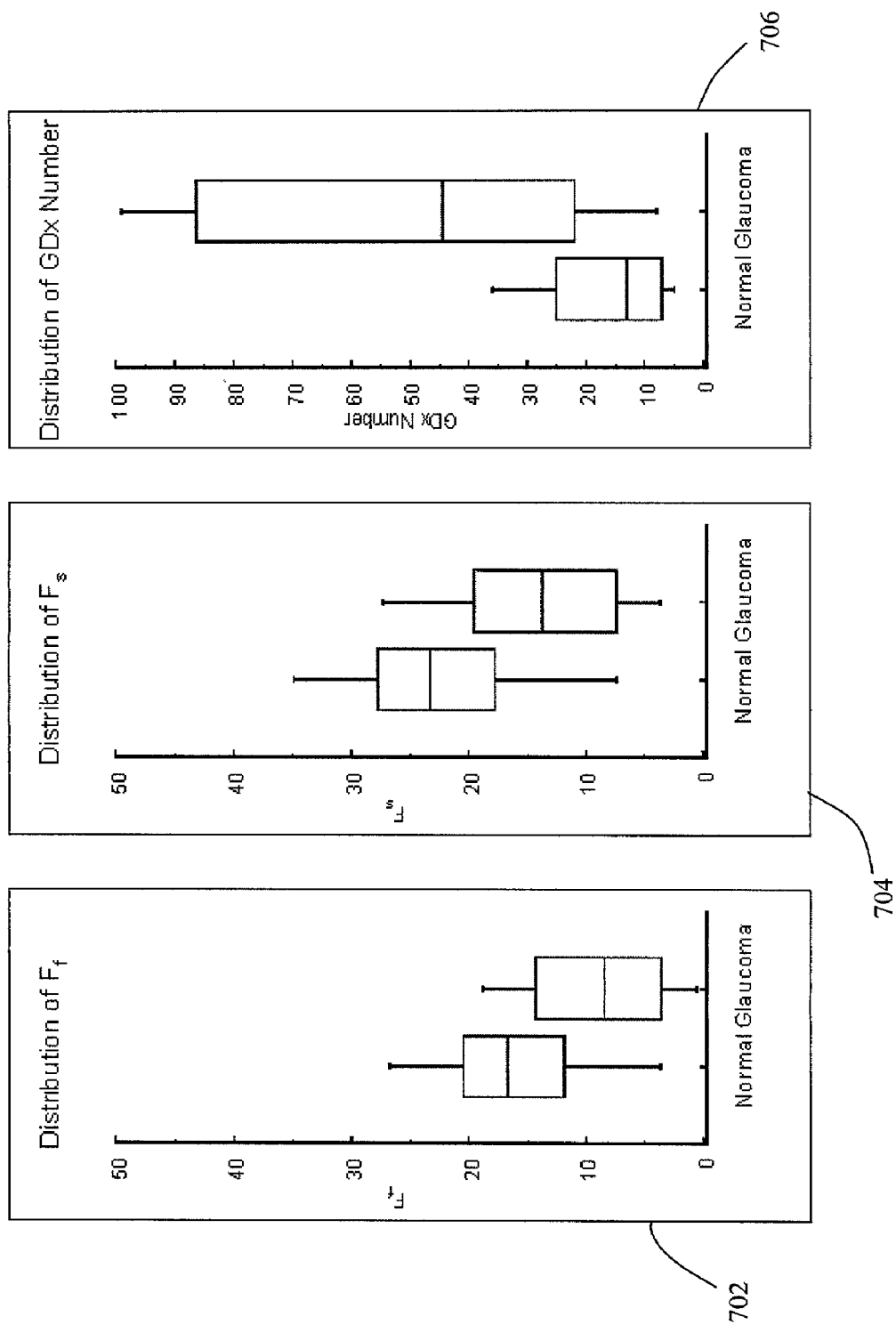
FIG. 7 shows a distribution of Fourier components and GDx numbers for normal and glaucomatous eyes.
Figure 8:
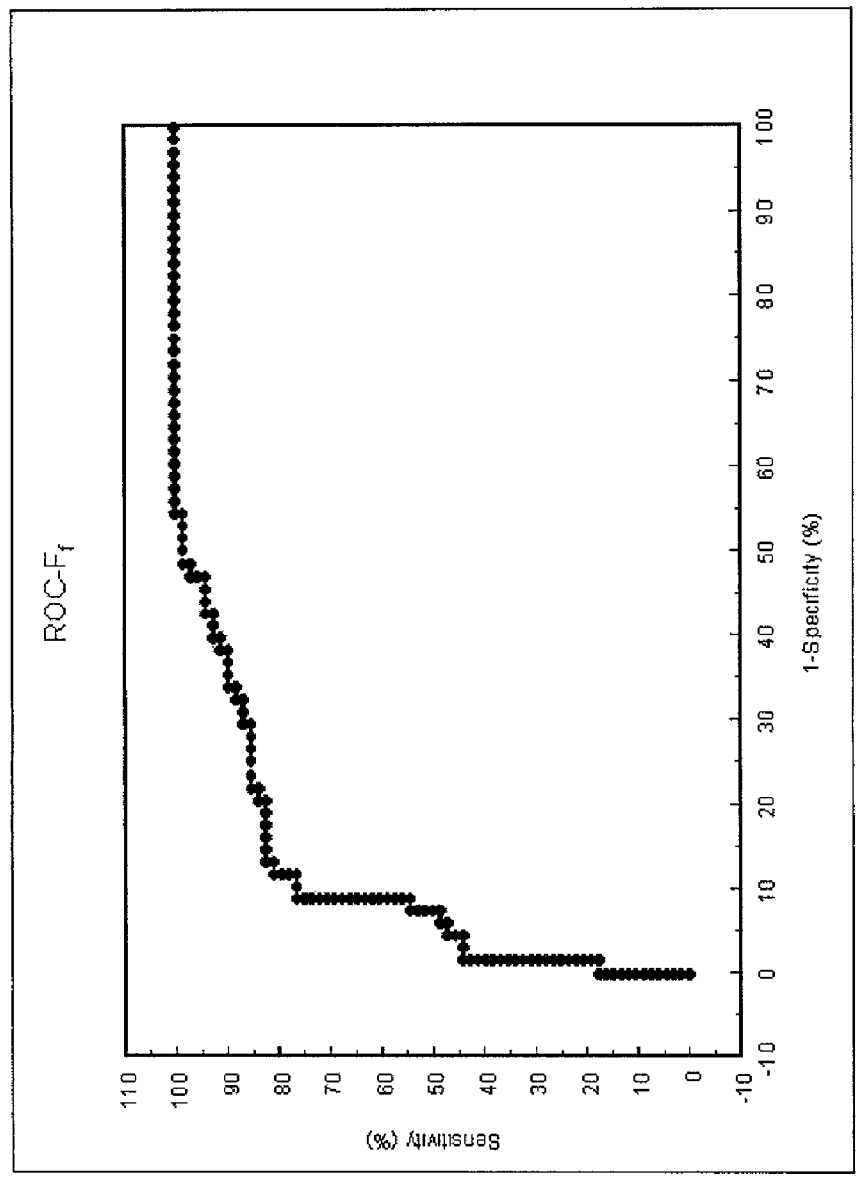
FIGS. 8, 9, and 10 show Receiver Operator Characteristic (ROC) curves for the measures shown in FIG. 7.

The first measure, the amplitude of the fundamental component ($F_{fund}$) is closely related to the size of the peak of the NFL distribution in a hemiretina but emphasizes (sinusoidal) shape as well. The smaller of the two hemiretina values was selected for this measure ($F_{fund}$) for each eye. The distribution of $F_{fund}$ for the normal and glaucomatous eyes are shown in the left panel of FIG. 7 at 702. As shown in FIG. 7, the amplitude of the fundamental is typically larger for normals than patients ($t_{(270)}$=13.86, p<0.0001). The ability of this Fourier measure to discriminate eyes with glaucoma from normal eyes was evaluated. FIG. 8 shows the Receiver Operator Characteristic (ROC) curve for this measure. The area under this ROC curve was 0.91 and the sensitivity and specificity values were 77% and 91%, respectively, with a cut-off of 10 (i.e., an eye was defined as glaucomatous if the Fourier fundamental was less than or equal to 10).

Figure 9:
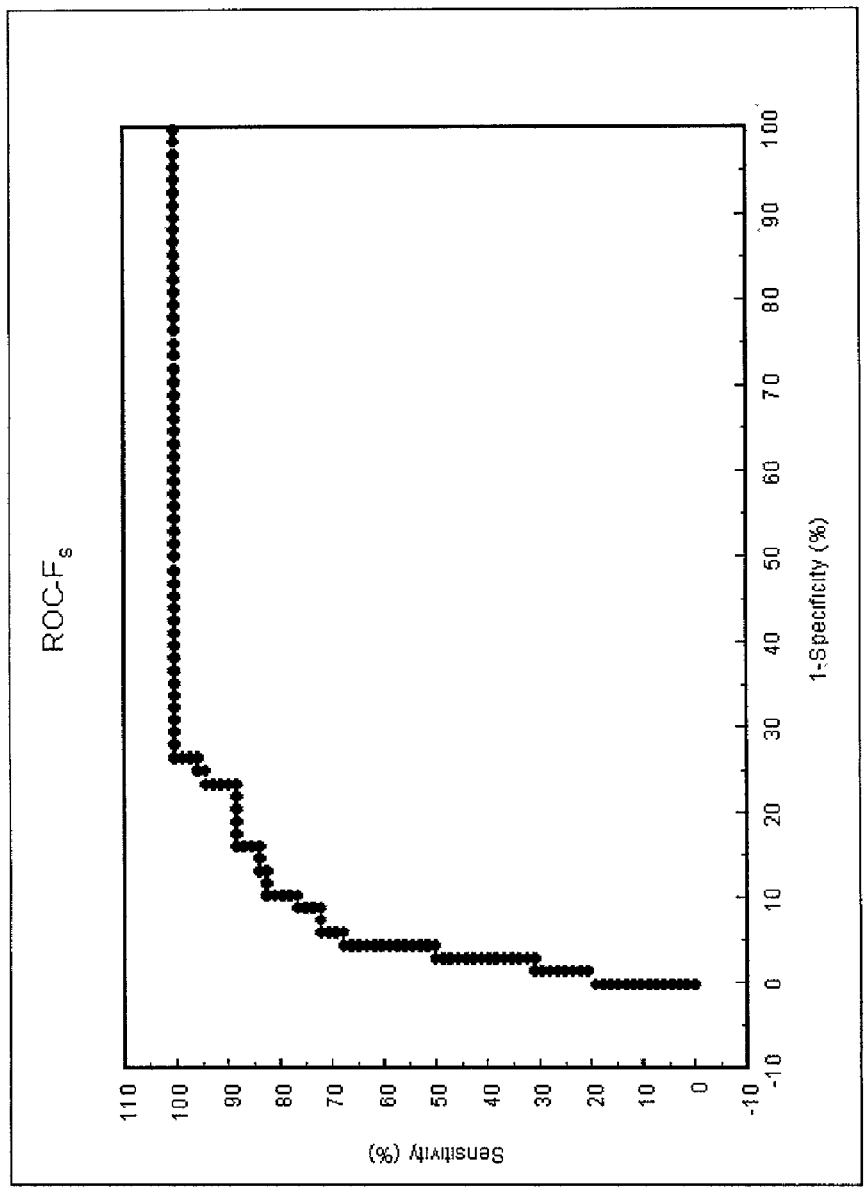

As previously described, loss of nerve fibers will not only lead to the reduction of the amplitude of the fundamental component, but also to the reduction of the amplitudes of higher frequency components (in the Fourier analysis, these components effectively "shape" the main hump provided by the fundamental component). A more detailed measure of shape characteristics, as indicated by Fourier analysis, is the sum of the amplitudes of the fundamental, second, third, and fourth harmonic coefficients. This sum ($F_{sum}$) was calculated separately for both hemiretinas and again, the smaller of the two values (for a given eye) was chosen for analysis. The distribution of $F_{sum}$ for the normal eyes and eyes with glaucoma is shown in the middle panel of FIG. 7 at 704. As with $F_{fund}$, $F_{sum}$ for normals was significantly higher than that for the patients ($t_{(270)}$=12.73, p<0.0001). A ROC curve (FIG. 9) was obtained for $F_{sum}$ to assess its ability to distinguish between normal and glaucomatous eyes. The area under the ROC curve was 0.90. Sensitivity and specificity values were 75% and 91%, respectively, with the cut-off of 15.7.

Since deviant values on either one of these measures ($F_{fund}$ or $F_{sum}$) might be indicative of NFL abnormalities, it is possible that the combination of these two measures would result in an increase in the sensitivity and specificity values obtained relative to those obtained with either measure alone. With the cut-offs set previously, 10 for the $F_{fund}$ component and 15.7 for $F_{sum}$, the sensitivity and specificity with this combined (by a logical OR) measure was 84% and 90%, respectively. The improvement shown by this combined measure is achieved in part because certain glaucoma patients not detected by one single measure alone are detected by the other measure when they are combined.

The sum of Fourier amplitudes, $F_{sum}$, reflects deviation from the normal shape of the hemifield's distribution of thickness values including aspects such as width of the peak and trough, shape of the rising and falling sides of the peak and trough, peak-to-trough amplitude, and others. However, since glaucoma often affects one eye more than the other, or one hemifield more than the other, consideration of an asymmetry in the Fourier measures between hemiretinas or between eyes, might improve their ability to separate glaucomatous eyes from normal eyes. Both types of asymmetry were considered, combining the Fourier measures ($F_{fund}$ and $F_{sum}$) with both a measure of symmetry between the hemifields of an eye and a measure of asymmetry between the eyes.

To reflect superior/inferior asymmetry within an eye, $F_{asymW/in}$ was used, which represents the difference between the Fourier sum ($F_{sum}$) for the superior and inferior hemiretinas. Looking at hemifield asymmetry in this way is similar to an anatomical analogue of the standard perimetry hemifield test. Eyes were defined as glaucomatous if the $F_{asymW/in}$ was greater than or equal to 6.2, but to avoid including eyes with an asymmetry due to a greater than normal amount of nerve fibers, at least one $F_{sum}$ value (either superior or inferior value) was required to be less than 19. In other words, this second constraint helps to limit the evaluation of asymmetries to eyes with an asymmetrical disruption of nerve fiber thickness loss, as opposed to an asymmetrical distribution of "extra" fibers in normals.

The other type of asymmetry, asymmetry between eyes, was also incorporated into the composite measure. The difference between the DC component of corresponding hemiretinas of the right and left eyes was calculated and the larger (either superior or inferior) difference ($F_{asymBet}$) was taken. The DC measure was used because its asymmetry was greater than for the other Fourier measures. The DC, $F_{fund}$ and $F_{sum}$ measures differed by 7.7%, 21.5% and 13.9%, respectively, on average, between the two eyes for normals, and 15.2%, 69.3%, and 35.3% respectively for glaucoma patients. Both eyes were classified as glaucomatous if the $F_{asymBet}$ was greater than 6 and one of their $F_{fund}$ values (from either the superior or inferior hemiretina, depending on which comparison was used for the $F_{asymBet}$ measure) was less than 11. Again, as with the asymmetry measure within eyes, this second constraint was incorporated to make sure the asymmetry was due to nerve fiber loss and not due to the "extra" fibers of one eye of a normal pair of companion eyes associated with the normal variation commonly found between eyes of normal individuals.

When all four of the Fourier measures were combined (with the same cut-offs as reported above) into one composite measure the sensitivity and specificity for the subjects was 96% and 90% respectively. That is, the combined measure considers asymmetry between the eyes ($F_{asymBet}$), between hemiretinas within eyes ($F_{asymW/in}$), as well as the amplitude of the fundamental ($F_{fund}$), and the sum of the amplitudes of the fundamental, first, second, third and fourth harmonics ($F_{sum}$), and yields good sensitivity and specificity.

The group of patients used in the current study contained some patients (14 eyes) who had advanced field loss (see Methods). With the exclusion of these fourteen eyes, the sensitivity was 94.4%, indicating that the high sensitivity is not due to the sample characteristics.

Figure 10:
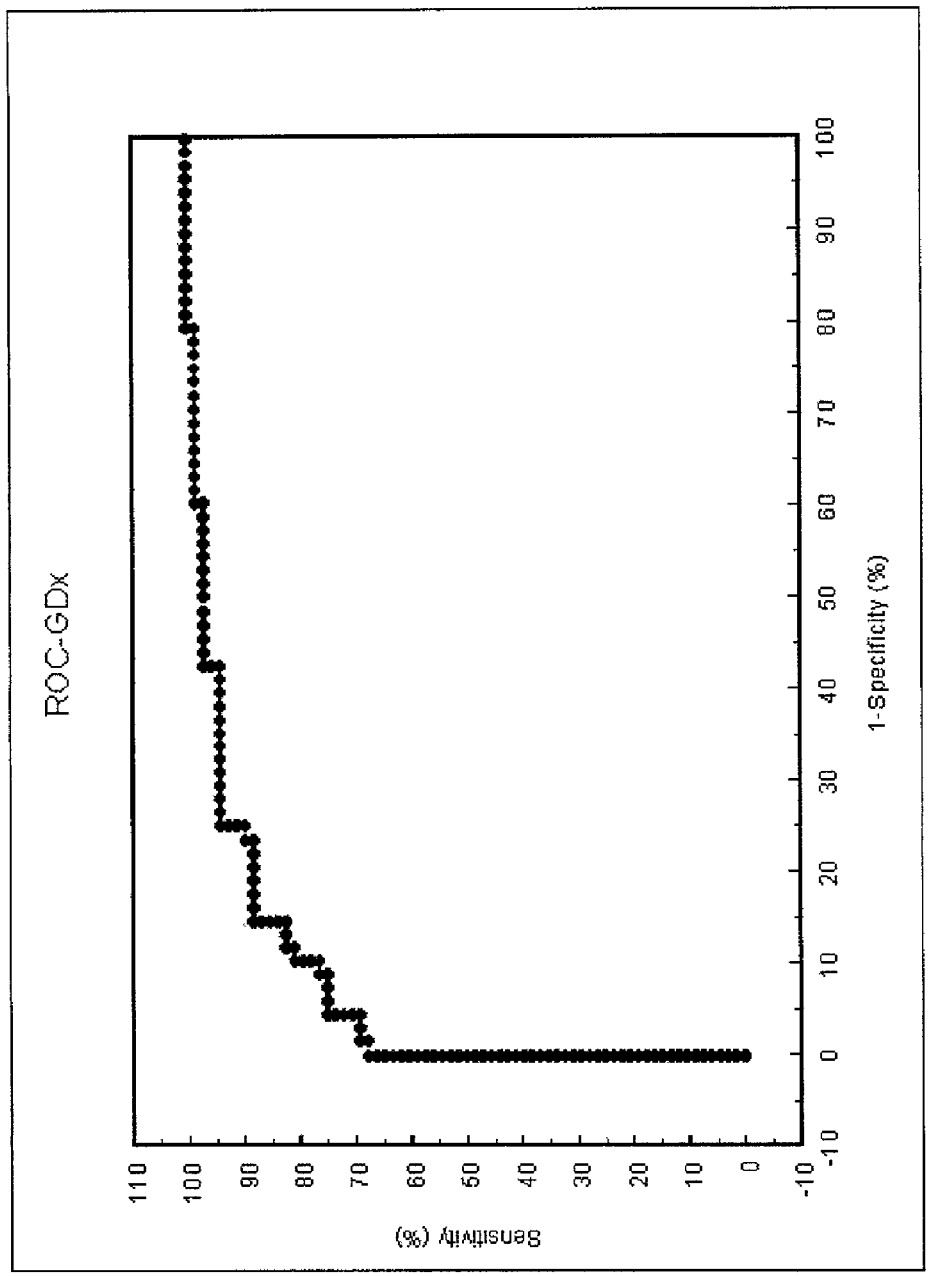

The GDx® software (LDT, Inc.) calculates fifteen measures based on the retardation map created by the scanning laser polarimeter. One of those fifteen is a GDx® number calculated by training a neural network based on the retardation values at all pixels. The GDx® number ranges from 0 to 100, with 100 indicating advanced glaucoma and 0 indicating completely normal. The distribution of the GDx® number for the normals and patients in the sample is shown in the right panel of FIG. 7 at 706 for comparison. Like the $F_{fund}$ and $F_{sum}$ measures, the GDx® number for the normals was significantly less than that for the patients ($t_{(134)}$=−10.55, p<0.0001). An ROC curve was constructed based on the GDx® number (FIG. 10). The area under the ROC curve for the GDx® number was 0.90. Taking a low, medium, and high cutoff of 15, 20, and 25 respectively, the sensitivity and specificity for the GDX® number is 96% and 63%, 76.5% and 89.7%, and 75% and 85% respectively. Thus, the sensitivity and specificity values obtained with the combination of the four Fourier measures was higher than that obtained with the GDx® number as well as these single Fourier measures used alone.

Figure 11:
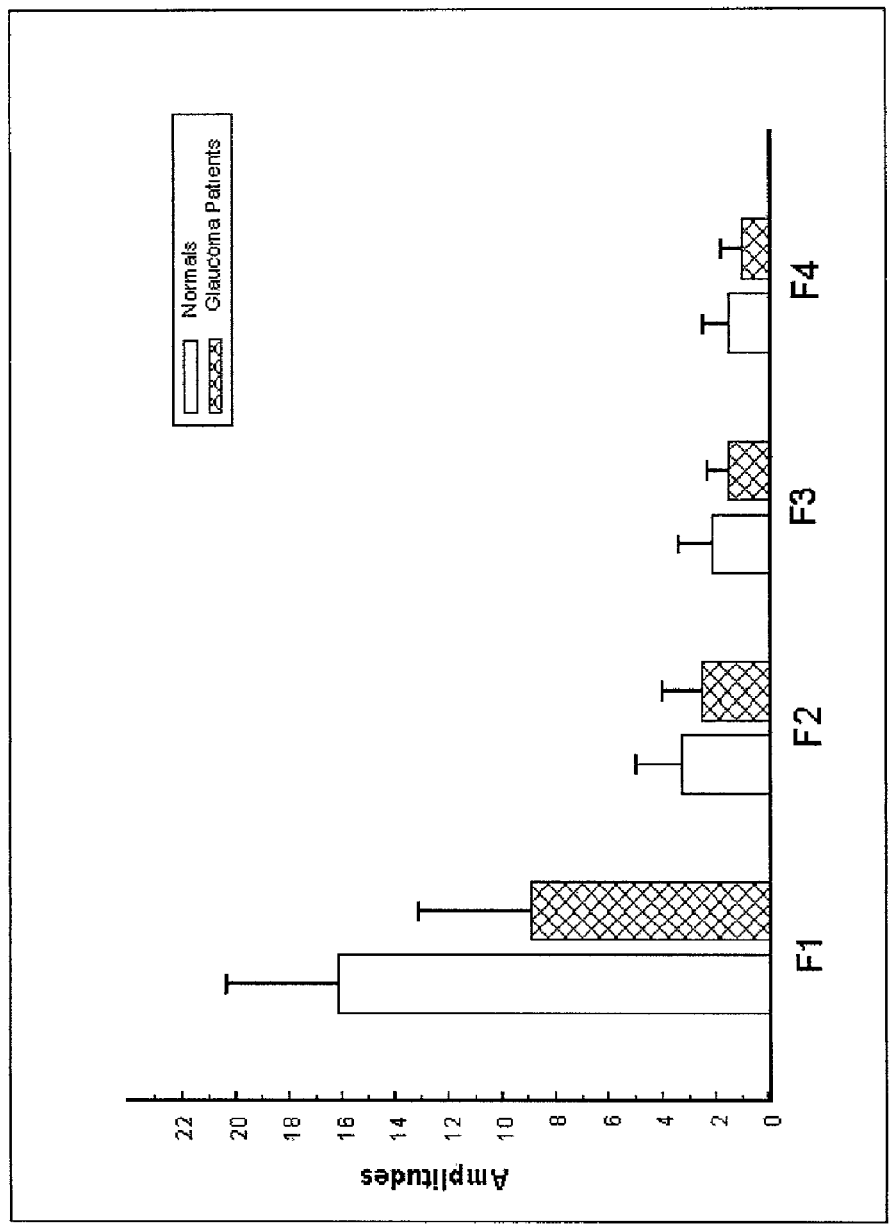
FIG. 11 shows Fourier components for both normal and glaucoma patient groups.

To consider the variation in shape of the nerve fiber thickness pattern (i.e., the "double-hump" pattern) further, the relation of the amplitudes of the fundamental, second, third and fourth harmonic components was considered for each individual. The pattern of the amplitudes of the four Fourier components (FIG. 11) differed significantly between the normal and glaucoma patient groups ($F_{(3,64)}=22.4$, $p<0.001$). No significant differences were found for either which hemifield was considered (superior or inferior), or which eye was considered ($p>0.05$). To quantify the relation of these coefficients, the values of the fundamental, second, third, and fourth harmonics for the patient and normal groups were normalized by dividing each by the magnitude of the fundamental for the respective group. This procedure shows that for the normal group the four Fourier harmonics were in the ratio of 1.0:0.23:0.14:0.10, whereas for the glaucoma patients they were in the ratio of 1.0:0.38:0.22:0.16. This suggests that aside from the fundamental, the primary difference between the glaucoma and normal groups is the $2^{nd}$ harmonic.

Discussion

A new approach to analyzing polarimetry data is able to discriminate effectively between normal and glaucomatous NFL patterns. The approach utilizes Fourier analysis of thickness measurements and creates a measure that emphasizes the pattern of the distribution of thickness measurements as defined by certain Fourier components. This measure is a composite of: the power of the fundamental Fourier component; the summed power of the first four Fourier components; superior/inferior asymmetry in the distribution of thicknesses (i.e., in the Fourier harmonics, $F_{sum}$); and the interocular asymmetry in mean level of the Fourier waveform (the DC component). Deviance on any one component classifies the eye as glaucomatous. The Fourier measures ($F_{fund}$ and $F_{sum}$ combined) appear to offer some improvement over the standard GDx® number; they also offer the advantage that they are direct (i.e., a direct analysis of the single factor, shape) and easier to interpret than a weighted combination of 15 factors (as in the calculation of the GDx Number). In addition, the Fourier measures offer promise for future development as a normal "template" shape and a metric of deviation from this normals' template which might allow the detection of local NFL defects. When combined with measures of intraocular and interocular asymmetry of the Fourier measures, the sensitivity and specificity are further improved.

A limitation of this study arises from the fact that the sensitivity and specificity values were determined from the same sample used to derive the criteria for discrimination. Thus the high sensitivity and specificity values likely overestimate the discriminability of the measures on an independent sample. In order to measure the degree of overestimation or bias, a split-half technique was performed where the sample was divided into 2 groups (each group contained half the normals and half the patients randomly selected). In the first sample the cut-off values were optimized and a sensitivity and specificity of 94% and 91% were achieved, respectively (new cut-off values were 6 for $F_{fund}$, 8 for $F_{sum}$, 6 for $F_{asymW/in}$ with a $F_{sum}$ below 20, and 3 for $F_{asymBet}$ with a $F_{fund}$ below 11). These cut-offs were then used on the second sample yielding a sensitivity and specificity of 94% and 88% respectively.

This split-half technique suggests the discriminability of the Fourier measures is robust over independent samples.

The methods in this study were applied to each eye to characterize eyes as normal or glaucomatous. An alternative method would have been to apply the measures to each pair of eyes and to classify individuals as normal or glaucoma patients, especially since one measure ($F_{asymBet}$) is based on an interocular comparison. A per individual method would, of course, generally tend to increase sensitivity of a measure given the additional chance (two eyes) to obtain a deviant value. Indeed, applying the same measures with the same cut-offs on a per individual, as opposed to per eye, basis resulted in a sensitivity and specificity of 94% and 82%, respectively, of the composite measure.

Another important factor to consider is the severity of glaucomatous disruption present in the patients used in the analysis. For example, in this study, only fourteen eyes were classified as having advanced field loss. Furthermore the sensitivity for patients with early or moderate field loss (i.e., with those 14 advanced eyes omitted) was still 94%. Thus, the Fourier measures performed well with patients with mild or moderate field loss.

Study Number 2: Applying Measures from one Population to other Populations

This study examines the question of whether measures derived from one data set retain their robustness when applied to new data sets obtained from different devices and populations. A discriminant analysis of the Fourier coefficients is also used.

This study evaluates two analytical methods that utilize Fourier analysis of NFL thickness estimates to detect glaucoma. Both methods were optimized for each of three individual data sets. The robustness of these methods was then assessed by applying each method (with optimized parameters or cut-offs from each data set) to the other data sets. Results are compared to other analysis methods.

Three independent data sets were utilized. Normals had undergone ophthalmologic examinations which revealed no evidence of glaucomatous optic neuropathy. Glaucoma patients were defined according to standard conventions by their referring ophthalmologist. Both eyes were used for all individuals. The three data sets were from the University of Louisville (UL), the University of Washington (UW), and Laser Diagnostic Technologies (LDT). The distribution of normal eyes to glaucomatous eyes were as follows:

| | | |
|---|---|---|
| University of Louisville: | 60 Normal Eyes | 54 Glaucomatous Eyes |
| University of Washington: | 82 Normal Eyes | 76 Glaucomatous Eyes |
| Laser Diagnostic Technologies: | 238 Normal Eyes | 212 Glaucomatous Eyes |

Retinal Imaging

NFL thickness estimates were obtained using three scanning laser polarimeters from Laser Diagnostic Technologies, Inc., San Diego, Calif. The thickness estimates obtained were then subjected to a Fourier analysis. Input data were the thickness estimates for 32 sectors located radially around the optic disc at 1.7 disc diameters (standard software output). The Fourier coefficients were then utilized in the two analysis methods (outlined below).

Figure 12:
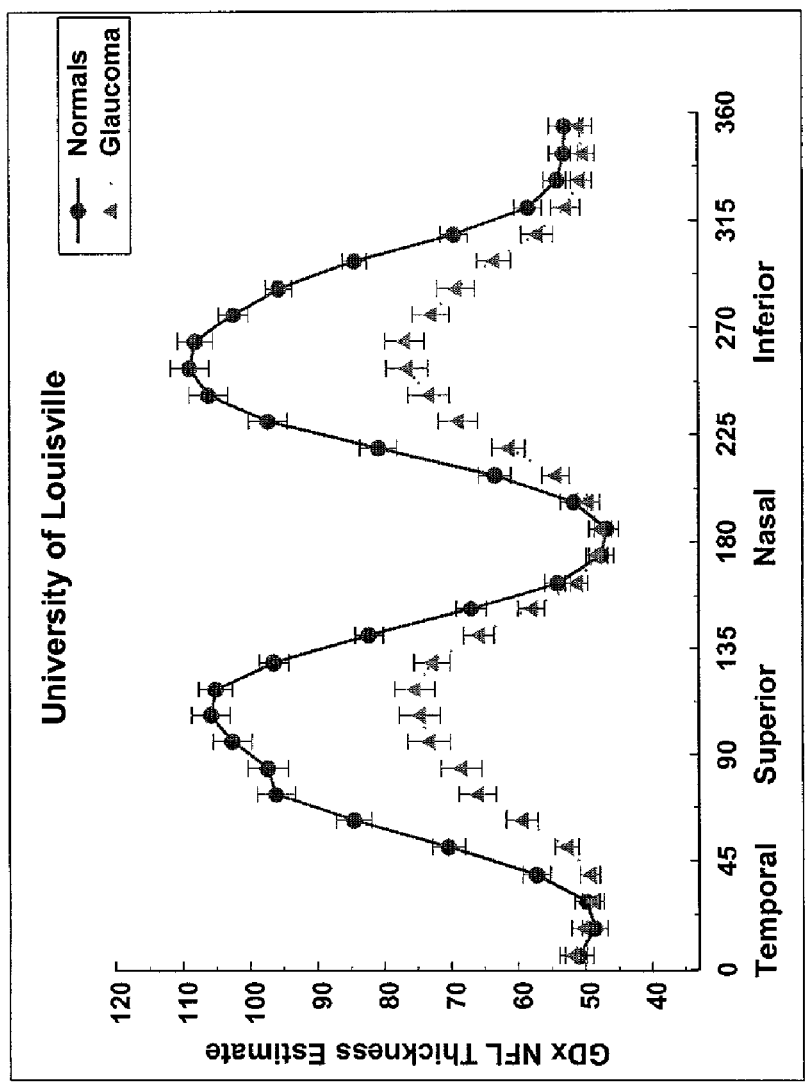
FIGS. 12, 13, and 14 show NFL thickness data for three sample populations.
Figure 13:
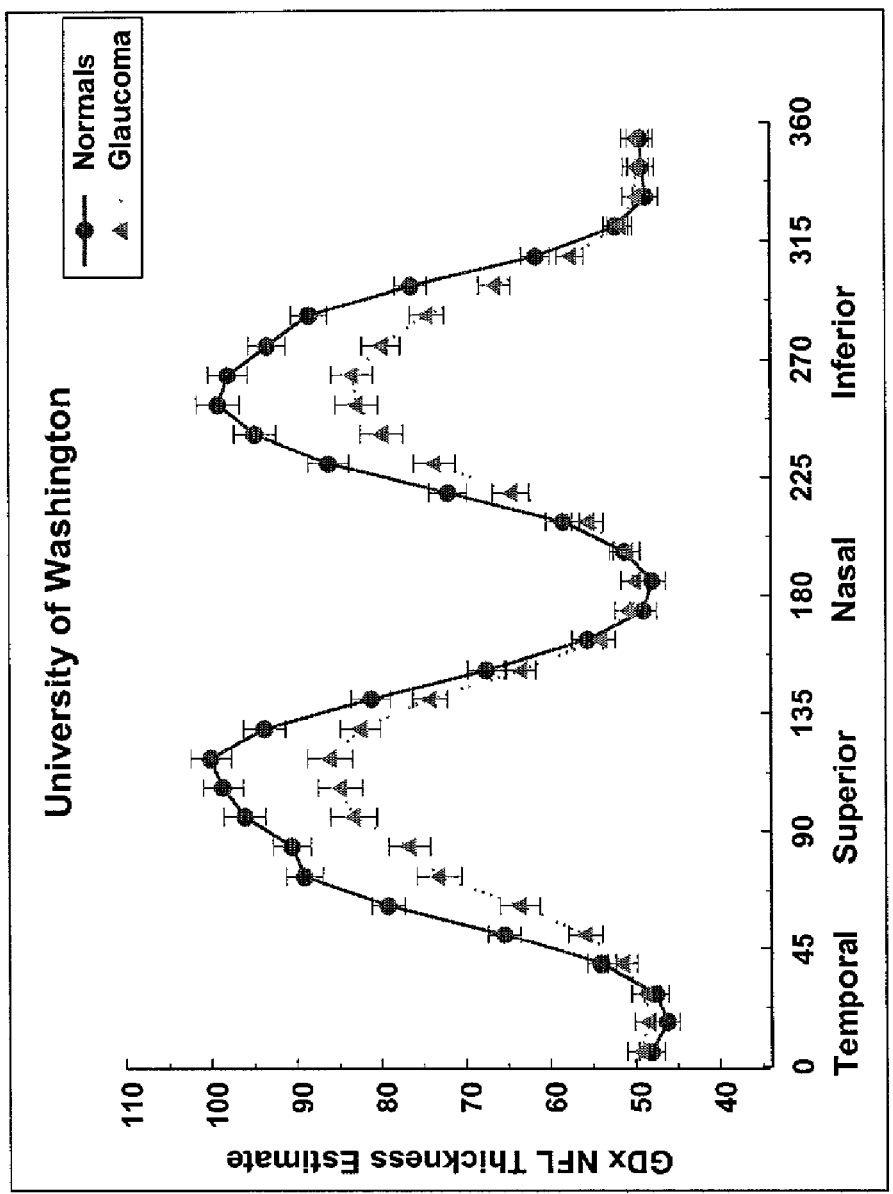
Figure 14:
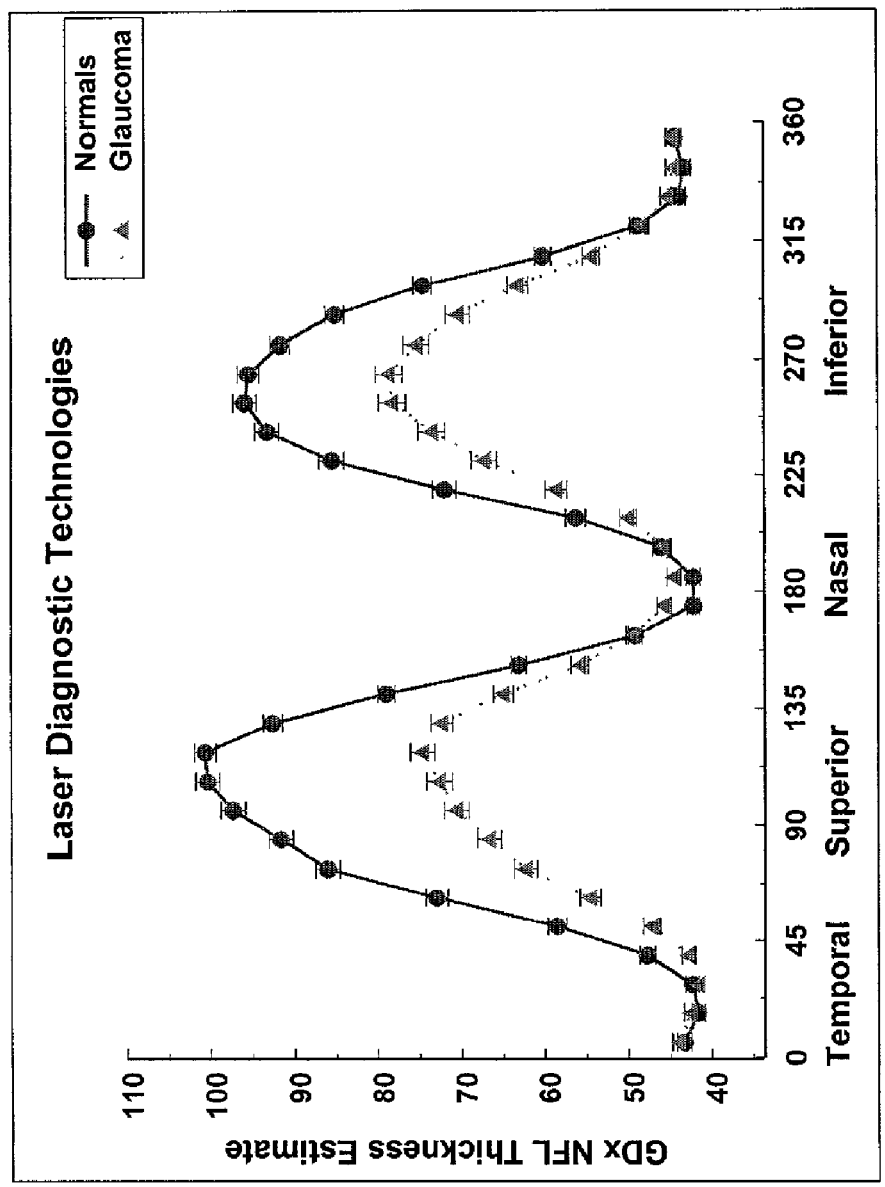
Figure 15:
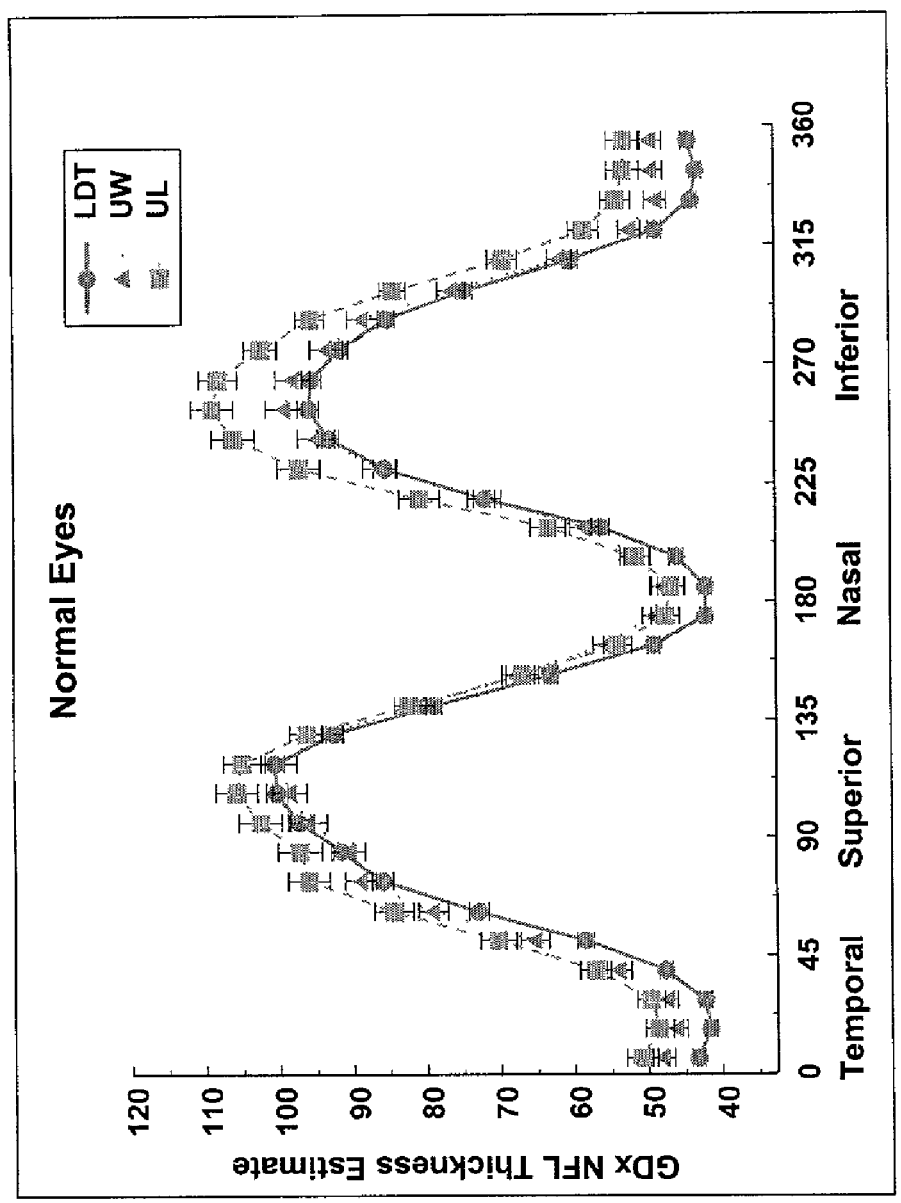
FIG. 15 shows NFL thickness data for the normal eyes shown in FIGS. 12, 13, and 14.
Figure 16:
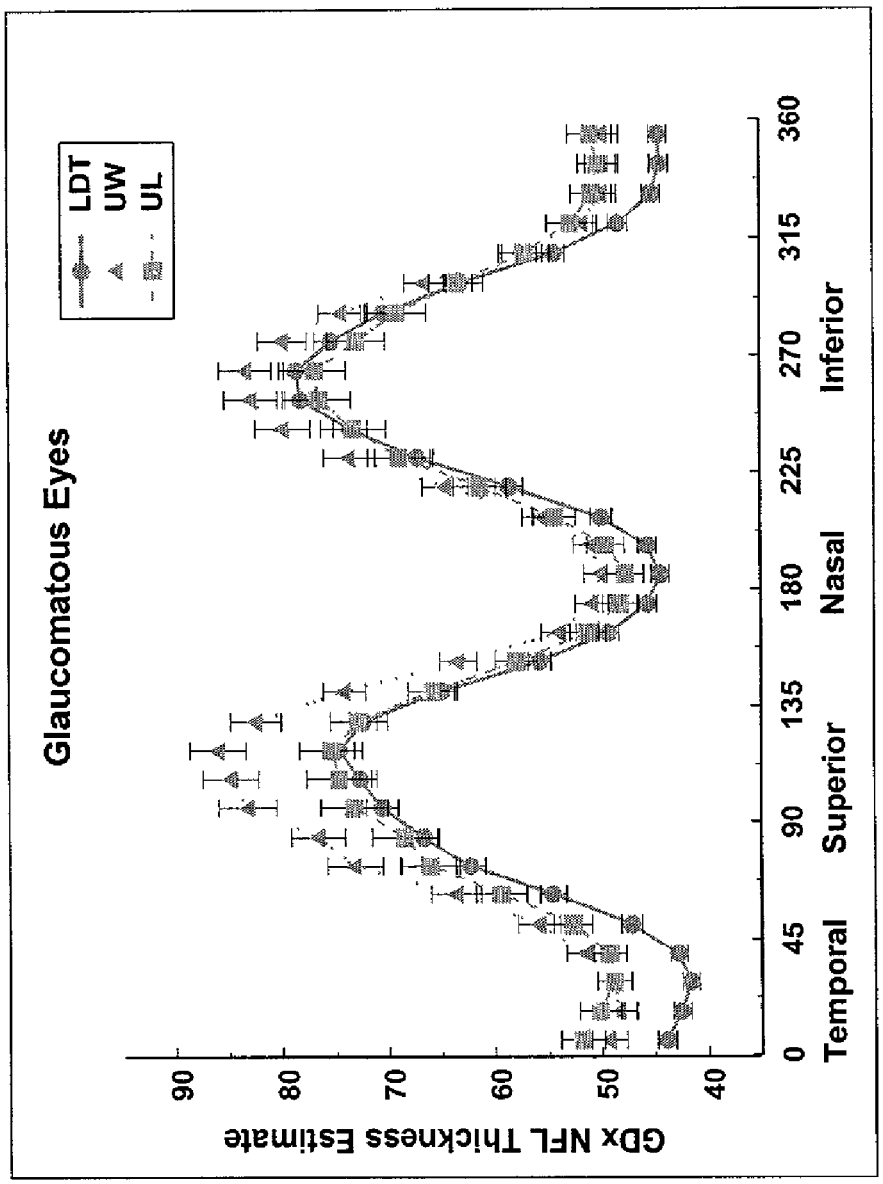
FIG. 16 shows NFL thickness data for the glaucomatous eyes shown in FIGS. 12, 13, and 14.

NFL thickness data for the three sample populations are shown in FIGS. 12, 13, and 14. FIG. 15 shows the normal eyes from all three data sets, and FIG. 16 shows the glaucomatous eyes from all three data sets.

Data Analysis

This study utilized a logical OR measure of discriminants as well as a stepwise discriminant analysis. The logical OR measure uses the Fourier amplitude coefficients taken by performing an analysis by hemiretina (superior and inferior separately). The coefficients are then combined in different ways to create several tests that are applied to the data in a manner similar to that discussed in study number 1, above. Cut-off values were optimized and the tests were combined by a logical OR operation; an individual was then classified as glaucomatous if they 'fail' any of the established tests (i.e., their measure is below cut-off value). There are four tests that were combined by logical OR:

Test 1. F1: This test uses the fundamental coefficient by itself.

Test 2. Fsum: This test sums all the coefficient values together.

Test 3. FasymW: This test uses the difference between the superior retina and inferior retina Fsum values (as long as one value is above a specified amount).

Test 4. FasymB: This test takes the difference between the DC value between the two eyes (for both superior retina and inferior retina). A second stipulation is that at least one Fundamental measure was above a criterion amount).

The linear discriminant function approach uses the Fourier amplitude and phase coefficients obtained from a full retinal analysis (not hemiretina). An asymmetry measure is calculated based on a ratio between the two eyes for each coefficient value. For example, the ratio of second harmonic amplitude coefficients is referred to as "$asyF2_{Amplitude}$," and the ratio of ninth harmonic phase coefficients is referred to as "$asyF9_{Phase}$." Then all coefficients and phase values along with the between-eye asymmetry measures were entered into a stepwise discriminant analysis and linear discriminant functions of the significant terms were generated. A ROC curve analysis was then performed using these functions.

The linear discriminant functions generated for each data set are as follows:

UL Data: $0.27(F2_{Amplitude})+0.29(F5_{Amplitude})+0.90(F9_{Amplitude})+0.46(asyF7_{Phase})-0.88(asyF9_{Phase})-0.60(asyF10_{Amplitude})+1.03(asyF11_{Amplitude})-0.76(asyF12_{Amplitude})-0.79(asyF13_{Phase})+1.31(asyF15_{Amplitude})-3.84$ UW Data: $0.22(F2_{Amplitude})+0.46(F5_{Amplitude})-0.17(F8_{Phase})-1.68(asyF2_{Amplitude})+4.18(asyF2_{Phase})+0.77(asyF7_{Amplitude})-0.91(asyF9_{Amplitude})+0.86(asyF11_{Amplitude})-0.53(asyF13_{Amplitude})-2.64$ LDT Data: $-0.02(DC_{Amplitude})-0.37(F1_{Phase})+0.21(F2_{Amplitude})+0.14(F3_{Amplitude})+0.26(F5_{Amplitude})-0.17(F5_{Phase})+0.50(F9_{Amplitude})-1.25(asyF2_{Amplitude})-0.43(asyF3_{Amplitude})-0.35(asyF4_{Phase})-0.48(asyF9_{Phase})+0.33(asyF11_{Amplitude})+0.41(asyF13_{Amplitude})-0.42(asyF15_{phase})+0.24(asyF16_{Phase})-0.79$ Results Table 2 shows the area under the ROC curve and the SEM for both Fourier analysis methods as well as for various other methods commonly used. Analysis methods used are the GDx 'Number' (based on a neural network analysis of the output parameters), a linear discriminant function based on three GDx output parameters (Weinreb, Zangwill, et al., Archives of Ophthalmology 1998), and four modulation parameters (Xu, Chen, Chen, Takahashi, Wang, and Mills, Journal of Glaucoma 1998). For the logical OR measure, a ROC analysis cannot be performed because different tests are combined in the procedure; therefore sensitivity and specificity are reported with specificity set at 90%.

Table 3 shows the area under the ROC curve and the SEM for the Fourier-based linear discriminant functions (LDF). Each LDF was derived using a given data set, and then these formulas were applied to each of the other data set to test for robustness. Shaded cells indicate the cases when a particular function was applied to the data set from which it was derived (same as Table 2.).

TABLE 3

Fourier LDF's Applied Across Data Sets

| | | Database LDF was derived from | | |
|---|---|---|---|---|
| | | UL | UW | LDT |
| Database | UL | .889 (.008) | .842 (.032) | .886 (.027) |
| LDF | UW | .782 (.038) | .937 (.018) | .807 (.035) |
| applied to | LDT | .849 (.018) | .816 (.02) | .943 (.011) |

Table 4 shows the sensitivity and specificity for the Fourier analysis method based on the logical OR combinatory procedure. The optimum cut-offs were derived using a given data set, and then these cut-offs were applied to each of the other data set to test for robustness. Shaded cells indicate the cases when the cut-offs were applied to the data set from which they were derived (same as Table 1.).

TABLE 4

Fourier logical OR tests applied to other data sets

| | | Database cur-off values were derived from | | |
|---|---|---|---|---|
| | | UL | UW | LDT |
| Database | UL | 95/90 | 61/72 | 81/80 |
| OR test | UW | 66/94 | 48/90 | 59/93 |
| applied to | LDT | 84/89 | 49/83 | 72/90 |

Discussion

The LDF based on Fourier measures relies on a variety of "shaping" components in addition to the $F2_{Amplitude}$ (which is similar to a peak-trough modulation measure). Prominent factors such as $F5_{Amplitude}$ and $F9_{Amplitude}$, and phase factors specify the shape of the NFL humps and can be important in this analysis. Asymmetries of phase and amplitude can also be important, presumably due to the asymmetric disruption of NFL shape in glaucoma.

The use of Fourier analysis to quantify the shape of the NFL estimates can provide the basis for new methods that

TABLE 2

Comparisons from ROC Analysis for Different Analytical Approaches

| | GDx Number | UCSD-LDF | Fourier-LDF | MxModS | MxModI | ReModS | ReModI | Fourier-OR |
|---|---|---|---|---|---|---|---|---|
| UL | .929 (.022) | .938 (.02) | .989 (.007) | .907 (.025) | .908 (.027) | .901 (.028) | .899 (.031) | 95/90 |
| UW | .80 (.034) | .825 (.032) | .937 (.018) | .81 (.035) | .818 (.033) | .818 (.035) | .819 (.033) | 48/90 |
| LDT | .892 (.015) | .892 (.016) | .943 (.011) | .888 (.016) | .798 (.021) | .887 (.016) | .809 (.021) | 72/90 | successfully discriminate normal from glaucomatous eyes. These methods can be more effective than current methods commonly used (average ROC area for the three data sets using Fourier-LDF was 0.96, see Table 2).

Study Number 3: Applying Measures to Two Data Sets from One Population

This study evaluates NFL thickness estimates taken from two retinal imaging devices for the use of accurately discriminating between healthy and glaucomatous eyes. The same subjects were imaged with the two retinal imaging devices. One eye was randomly imaged from each subject. Of 80 total eyes, 38 were healthy, and 42 were glaucomatous. Glaucoma was defined by repeatable abnormal visual fields (SAP) with either GHT results outside normal limits (99%) or a CPSD outside normal limits (95%).

Retinal Imaging

Estimates of NFL thickness were obtained using a scanning laser polarimeter (SLP) available from Laser Diagnostic Technologies, Inc., San Diego, Calif., and an ocular coherence tomograph (OCT) available from Zeiss-Humphrey, Dublin, Calif. Both devices provide NFL thickness estimates around the optic disc, however they operate using very different principles. The scanning laser polarimeter uses polarized light to infer thickness as measured by the change in polarization (retardation). Polarimetry measures used for this analysis were split up into 32 sectors located radially around the optic disc at a distance of 1.7 disc diameters.

The OCT infers thickness based on measurements of the time-course of backscattered light. Thickness estimates at 100 angles around a ring (3.4 mm diameter centered on the disc) were obtained which were then split into 12 sectors located radially around the optic disc.

Figure 17:
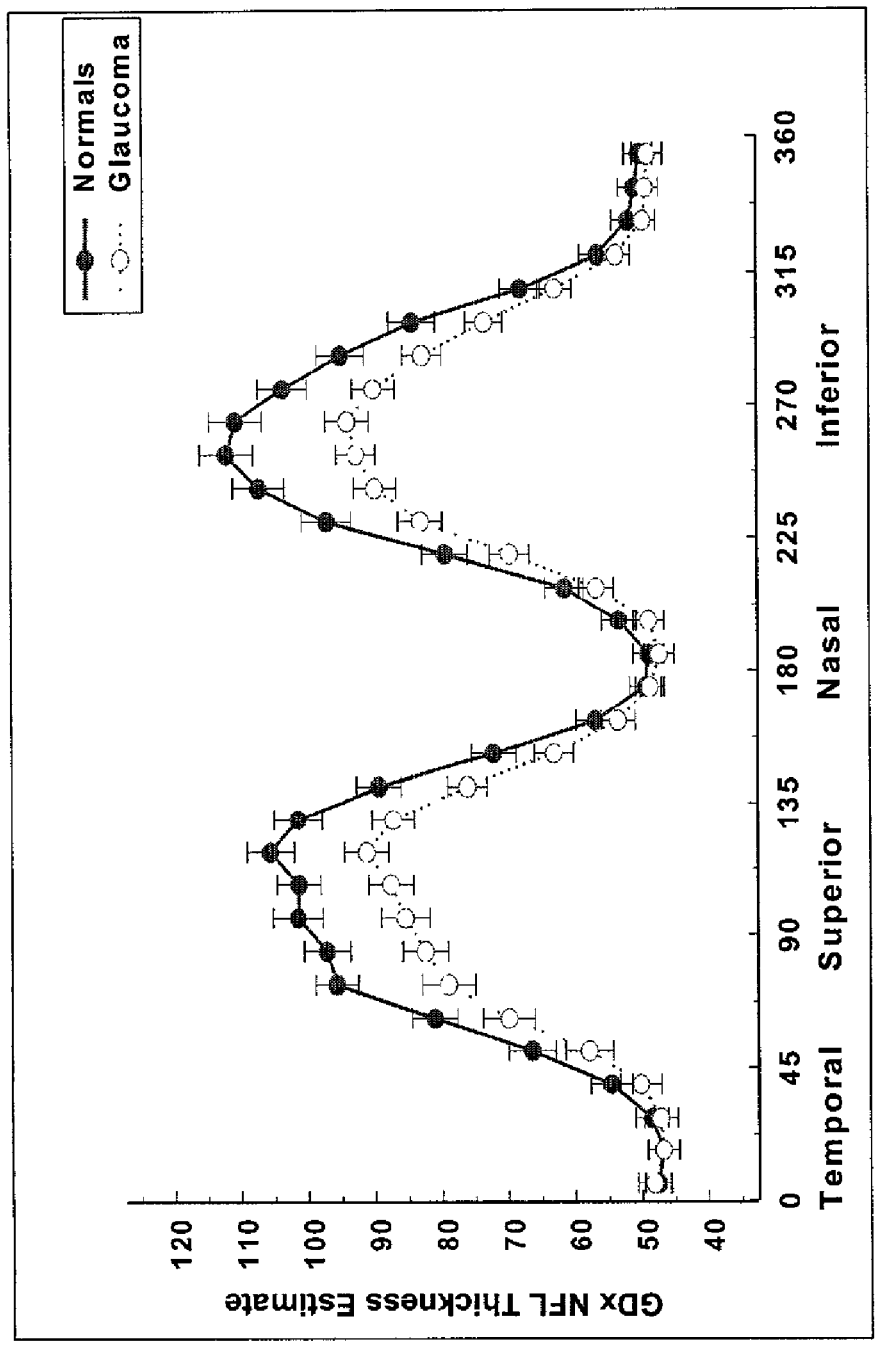
FIG. 17 shows NFL thickness data taken by a scanning laser polarimeter (SLP)
Figure 18:
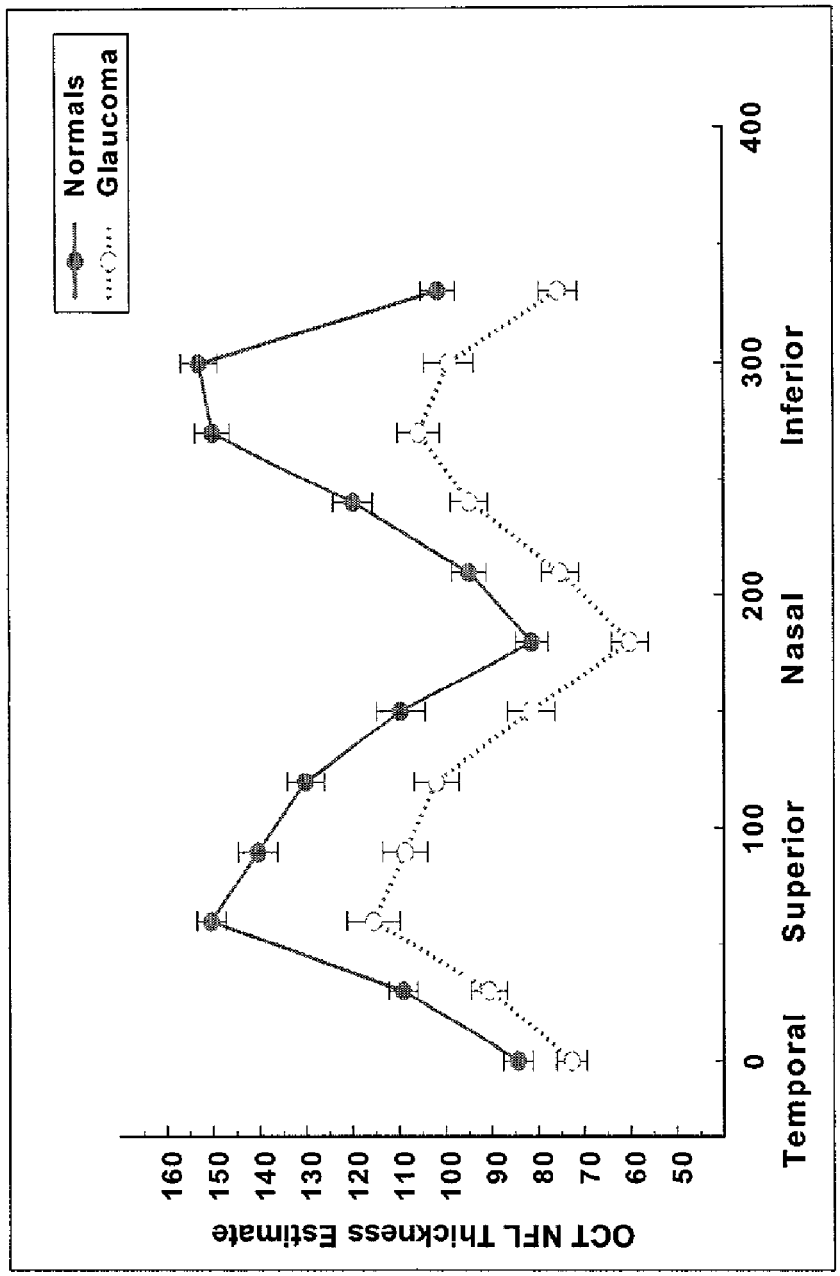
FIG. 18 shows NFL thickness data taken by an ocular coherence tomograph (OCT)
Figure 19:
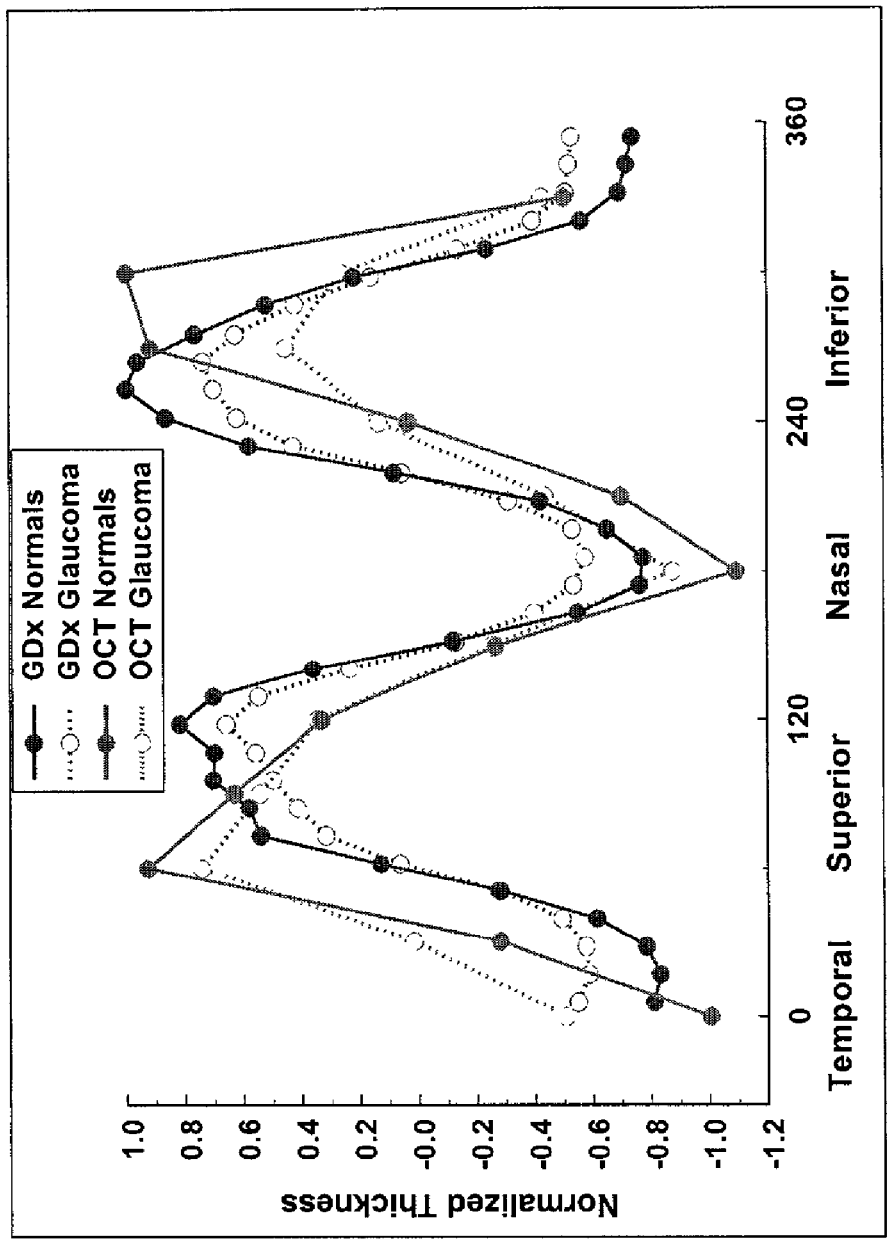
FIG. 19 shows data from FIGS. 17 and 18 normalized and plotted together.

NFL thickness estimates taken by the SLP device (also referred to as GDx data) are shown in FIG. 17, and NFL thickness estimates taken by the OCT device are shown in FIG. 18. FIG. 19 shows normalized data plotted together from both devices. The values were normalized for each curve by subtracting the curve's mean from each point, and then dividing the resulting value by the maximum value for each device.

Data Analysis

The same analysis and procedures were applied to both data types (GDx and OCT). First, a fast Fourier transform (FFT) was performed on the thickness estimates for each individual. The Fourier analysis provides coefficients indicating the amplitude and phase of each sine-wave frequency component that make up the wave-form being analyzed (the shape of the curve plotting the original data as a function of angle). The number of resulting components is equal to half the number of data points being analyzed.

A discriminant analysis was performed on the Fourier coefficients (amplitude and phase values) and linear discriminant functions were generated. This analysis was performed separately on the GDx data and the OCT data. The discriminant functions were as follows:

GDx Data: $0.26(F2_{Amplitude})+1.37(F12_{Amplitude})+0.68(F12_{Phase})-1.91(F13_{Amplitude})+0.80(F14_{Phase})-5.94$ OCT Data: $0.04(DC)+0.08(F2_{Amplitude})+0.68(F3_{Phase})-6.58$ Results Sensitivity and specificity values for various methods of analysis are shown in Table 5. Specificity was set at a minimum of 70% (left side), and at a minimum of 90% (right side). For the GDx data, analysis methods used for comparison purposes are the GDx 'Number' (based on a neural network analysis of the output parameters), a linear discriminant function based on three GDx output parameters (Weinreb, Zangwill, et al., Archives of Ophthalmology 1998), and a discriminant function derived from the Fourier coefficients. For the OCT data, analysis methods used for comparison purposes are mean thickness, thickness at the inferior sector, and a discriminant function based on Fourier coefficients.

TABLE 5

| | Table from ROC data (Spec > 70%) | | | | Table from ROC data (Spec > 90%) | | |
|---|---|---|---|---|---|---|---|
| | Number | UCSD-LDF | Fourier-LDF | | Number | UCSD-LDF | Fourier-LDF |
| GDx | 63/71 | 71/71 | 97/71 | GDx | 47/90 | 47/90 | 82/90 |
| | Mean | Inferior | Fourier-LDF | | Mean | Inferior | Fourier-LDF |
| OCT | 92/71 | 97/71 | 95/71 | OCT | 71/90 | 58/90 | 76/90 |

Figure 20:
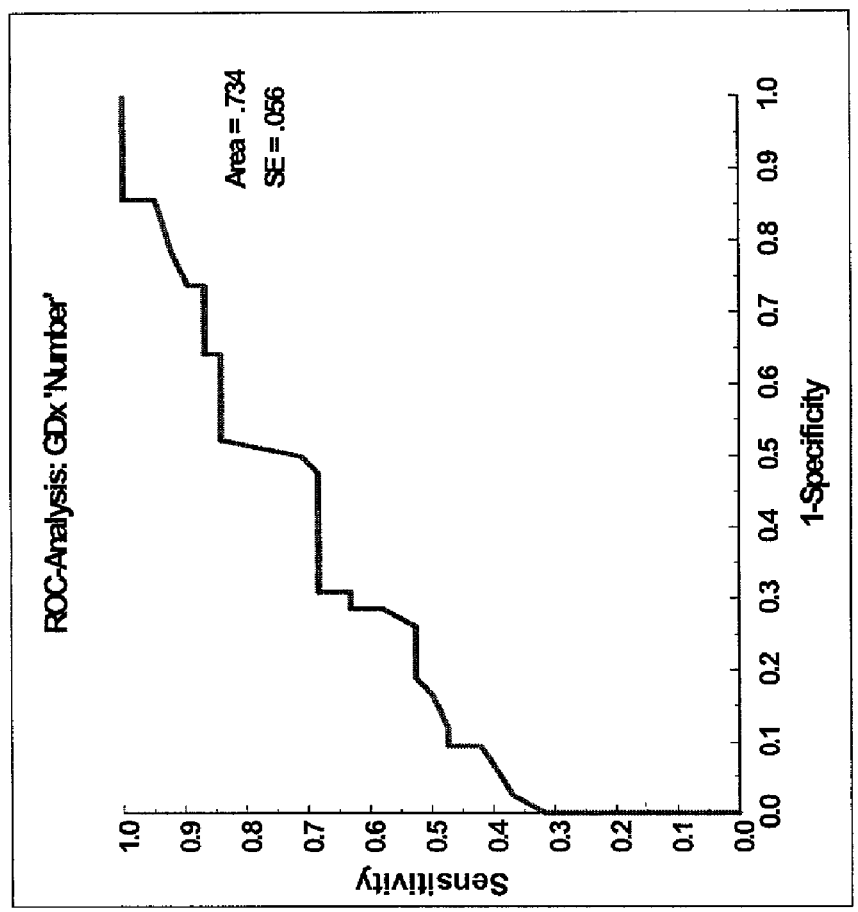
FIGS. 20, 21, and 22 show ROC plots for GDx data.
Figure 21:
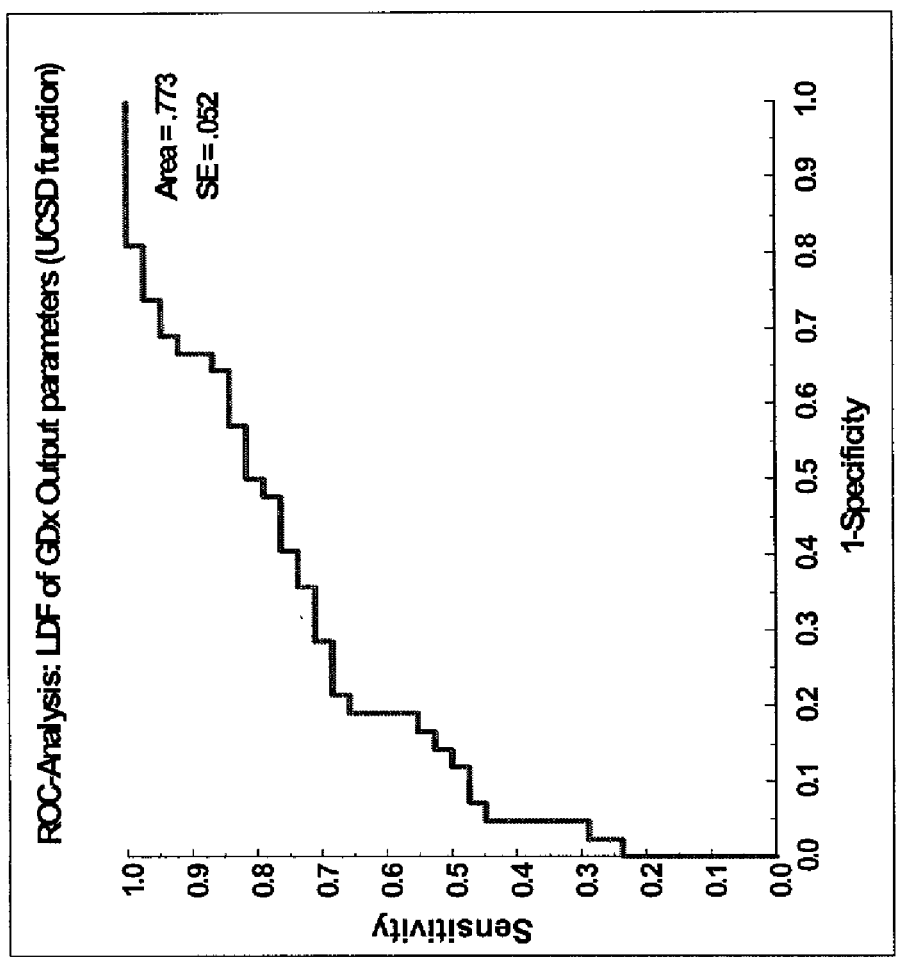
Figure 22:
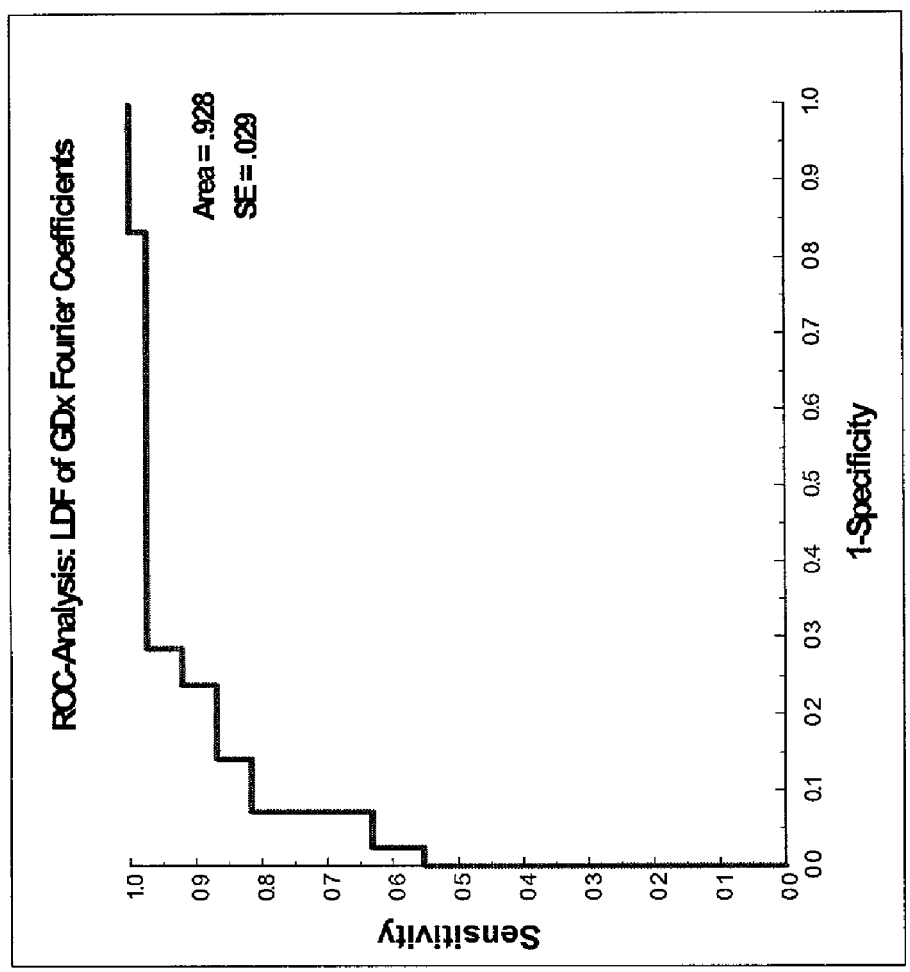
Figure 23:
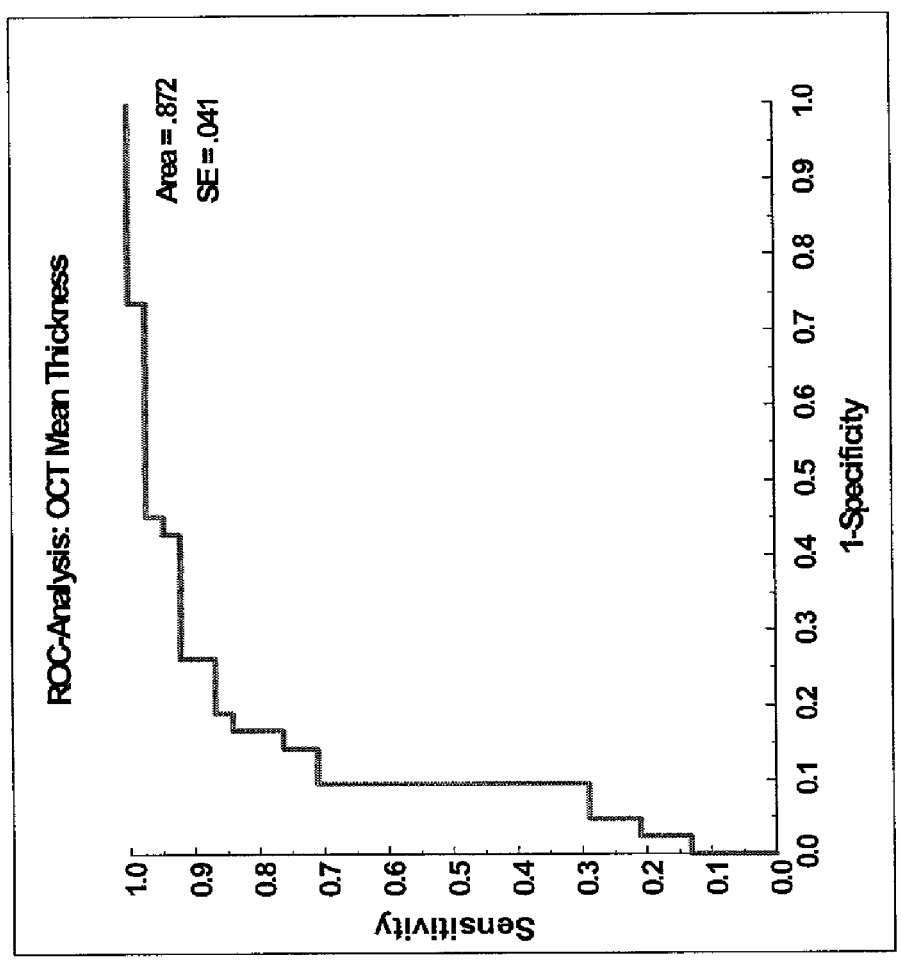
FIGS. 23, 24, and 25 show ROC plots for OCT data.
Figure 24:
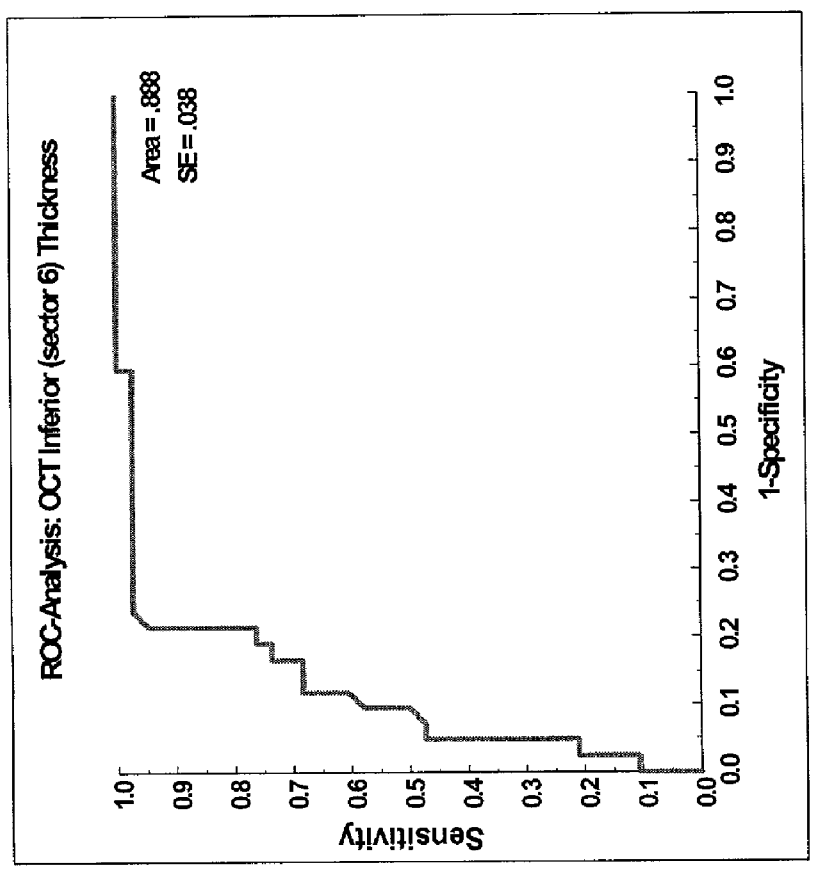
Figure 25:
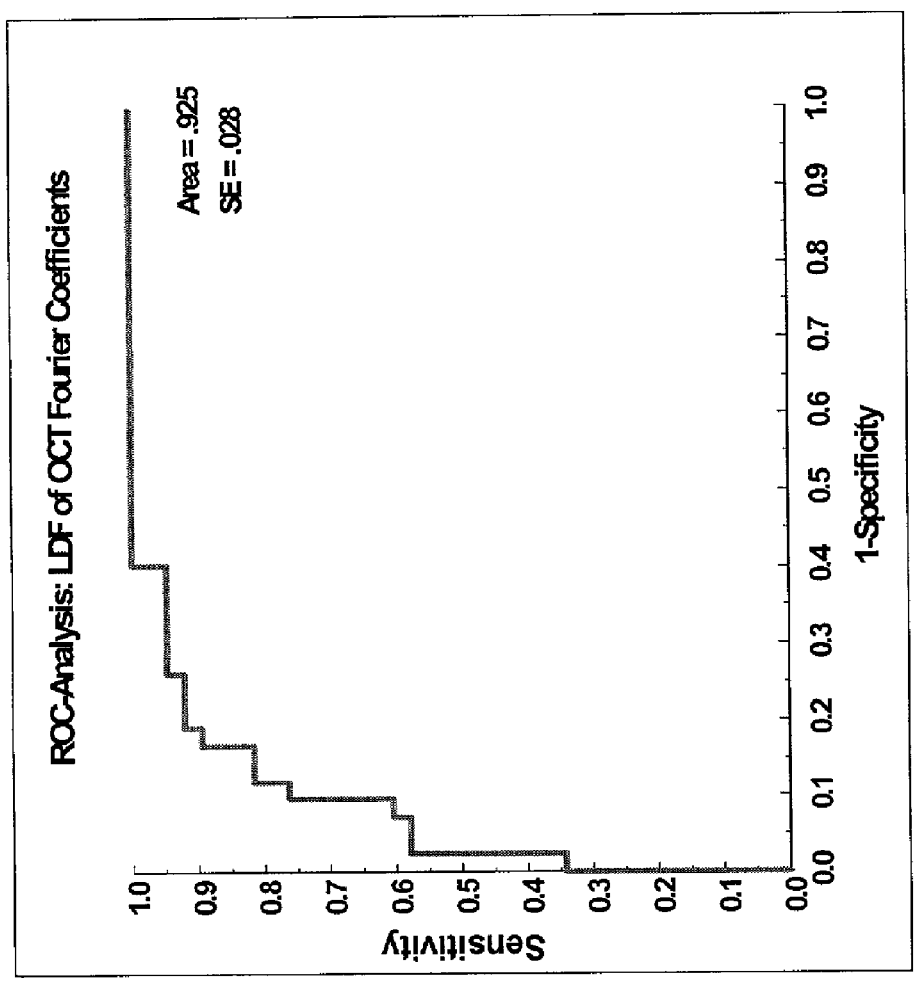

FIGS. 20, 21, and 22 show ROC plots for GDx data, and FIGS. 23, 24, and 25 show ROC plots for OCT data. The area under the curve and the standard error of the mean are given in each figure. For both GDx and OCT data, the Fourier analysis of the present invention provides superior results.

Discussion

OCT and GDx devices produce estimates of NFL thickness that differ is several important ways (FIGS. 17 and 18), yet both are analyzed effectively with the shape-based analysis provided by the methods and apparatus of the present invention. (See Table 5 and FIGS. 20–25).

Discriminant analysis of the Fourier components yields sensitivity and specificity that is higher than that obtained by analysis methods commonly used for either GDx or OCT devices.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method comprising:
receiving waveform data representing a shape of a surface;
determining a plurality of Fourier coefficient amplitudes and phase values corresponding to the waveform data;
entering at least one phase value into a discriminant measure; and
comparing a result of the discriminant measure against a threshold.

2. The method of claim 1 wherein the discriminant measure comprises an equation that includes the at least one phase value, and also includes at least one Fourier coefficient amplitude.

3. The method of claim 1 wherein the waveform data represents the shape of a nerve fiber layer in a hemiretina.

4. The method of claim 1 wherein the waveform data represents the shape of a nerve fiber layer in a ring around an entire retina.

5. The method of claim 1 wherein determining a plurality of Fourier coefficient amplitudes and phase values comprises performing a fast Fourier transform (FFT).

6. The method of claim 1 wherein determining a plurality of Fourier coefficient amplitudes and phase values comprises performing a discrete Fourier transform (DFT).

7. The method of claim 1 further comprising generating interocular asymmetry measures by taking a ratio of each Fourier coefficient amplitude from one eye to a corresponding Fourier coefficient amplitude from another eye.

8. The method of claim 7 wherein the discriminant measure comprises an equation that includes the at least one phase value, and also includes at least one interocular asymmetry measure.

9. The method of claim 1 further comprising generating intraocular asymmetry measures by comparing a sum of Fourier coefficient amplitudes from one hemiretina to a sum of Fourier coefficient amplitudes from another hemiretina.

10. The method of claim 9 wherein the discriminant measure comprises an equation that includes the at least one phase value, and also includes at least one intraocular asymmetry measure.

* * * * *